(12) United States Patent
Katsumura et al.

(10) Patent No.: US 11,759,998 B2
(45) Date of Patent: Sep. 19, 2023

(54) METHOD FOR PRODUCING GELATIN FORMED BODY AND GELATIN FORMED BODY

(71) Applicant: FUJIFILM Corporation, Tokyo (JP)

(72) Inventors: Manabu Katsumura, Ashigarakami-gun (JP); Takahiro Hiratsuka, Ashigarakami-gun (JP); Hideo Fushimi, Ashigarakami-gun (JP); Yoshio Ishii, Ashigarakami-gun (JP); Ai Okamura, Ashigarakami-gun (JP); Hiroshi Ota, Ashigarakami-gun (JP); Jun Arakawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 616 days.

(21) Appl. No.: 16/213,648

(22) Filed: Dec. 7, 2018

(65) Prior Publication Data

US 2019/0168444 A1    Jun. 6, 2019

Related U.S. Application Data

(63) Continuation of application No. PCT/JP2017/021124, filed on Jun. 7, 2017.

(30) Foreign Application Priority Data

Jun. 8, 2016   (JP) ................................. 2016-114252
Feb. 21, 2017  (JP) ................................. 2017-030322

(51) Int. Cl.
   B29C 64/112     (2017.01)
   B33Y 80/00      (2015.01)
   (Continued)

(52) U.S. Cl.
   CPC .......... B29C 64/112 (2017.08); *A61L 27/222* (2013.01); *A61L 27/3847* (2013.01);
   (Continued)

(58) Field of Classification Search
   CPC .......................... B29C 64/112; B29C 64/165
   See application file for complete search history.

(56) References Cited

U.S. PATENT DOCUMENTS

4,176,117 A * 11/1979 Oudem .................... C09H 1/04
                                                    530/355
5,080,292 A *  1/1992 Nishibori ................. C08J 3/12
                                                    241/21

(Continued)

FOREIGN PATENT DOCUMENTS

JP    2001-353787 A    12/2001
JP    2005-254534 A     9/2005
(Continued)

OTHER PUBLICATIONS

Extended European Search Report for European Application No. 17810344.6, dated May 15, 2019.
(Continued)

*Primary Examiner* — Matthew J Daniels
*Assistant Examiner* — Andrew L Swanson
(74) *Attorney, Agent, or Firm* — Birch, Stewart, Kolasch & Birch, LLP

(57) ABSTRACT

An object of the present invention is to provide a method for producing a gelatin formed body having a minimized content of a component harmful to a living body and high biocompatibility with high shaping accuracy, and a gelatin formed body produced by the method. According to the present invention, provided is a method for producing a gelatin formed body, the method including: a step a of forming, on a substrate, a layer containing a powder which is obtained by air-drying an aqueous gelatin solution and has an average particle diameter of 25 to 200 μm; and a step b of jetting liquid droplets of an aqueous solution containing alcohols having a boiling point of 120° C. or lower toward the layer formed in the step a from a nozzle and flying the (Continued)

jetted liquid droplets so that the liquid droplets are landed on the layer formed in the step a, thereby forming a gelatin formed body.

14 Claims, 15 Drawing Sheets

Specification includes a Sequence Listing.

(51) Int. Cl.
| | |
|---|---|
| *B33Y 10/00* | (2015.01) |
| *A61L 27/22* | (2006.01) |
| *A61L 27/56* | (2006.01) |
| *A61L 27/38* | (2006.01) |
| *B33Y 70/00* | (2020.01) |
| *B29C 64/188* | (2017.01) |
| *B29C 64/209* | (2017.01) |
| *A61L 27/50* | (2006.01) |
| *C07K 14/47* | (2006.01) |
| *C12M 1/00* | (2006.01) |
| *B29L 31/00* | (2006.01) |
| *C07K 14/78* | (2006.01) |

(52) U.S. Cl.
CPC ............... *A61L 27/50* (2013.01); *A61L 27/56* (2013.01); *B29C 64/188* (2017.08); *B29C 64/209* (2017.08); *B33Y 10/00* (2014.12); *B33Y 70/00* (2014.12); *B33Y 80/00* (2014.12); *A61L 2430/02* (2013.01); *B29L 2031/7532* (2013.01); *C07K 14/47* (2013.01); *C07K 14/78* (2013.01); *C12M 1/00* (2013.01)

(56) References Cited

U.S. PATENT DOCUMENTS

| | | | | |
|---|---|---|---|---|
| 5,225,536 | A | * | 7/1993 | Nishibori ............... C08J 3/122 521/61 |
| 6,454,811 | B1 | * | 9/2002 | Sherwood ............... A61F 2/28 623/23.72 |
| 2003/0114936 | A1 | * | 6/2003 | Sherwood ........... A61F 2/30942 623/23.58 |
| 2005/0003189 | A1 | * | 1/2005 | Bredt .................... B33Y 70/00 428/402 |
| 2007/0181239 | A1 | | 8/2007 | Yamazawa et al. |
| 2007/0202191 | A1 | | 8/2007 | Borden |
| 2010/0247938 | A1 | | 9/2010 | Abe et al. |
| 2012/0165263 | A1 | | 6/2012 | Hiratsuka et al. |
| 2016/0040025 | A1 | * | 2/2016 | Norikane ............. C09D 103/02 106/157.2 |
| 2016/0067917 | A1 | | 3/2016 | Hirata et al. |

FOREIGN PATENT DOCUMENTS

| | | |
|---|---|---|
| JP | 2009-102526 A | 5/2009 |
| JP | 2009-528090 A | 8/2009 |
| JP | 2010-228103 A | 10/2010 |
| JP | 2010-228316 A | 10/2010 |
| JP | 2016-37041 A | 3/2016 |
| JP | 2016-55531 A | 4/2016 |
| WO | WO 2005/11536 A1 | 2/2005 |
| WO | WO 2011/027850 A1 | 3/2011 |

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2017/021124, dated Dec. 20, 2018, with English translation.
International Search Report (Form PCT/ISA/210) for International Application No. PCT/JP2017/021124, dated Jul. 25, 2017, with English translation.
Korean Office Action, dated Apr. 13, 2020, for corresponding Korean Application No. 10-2018-7035556, with an English translation.

* cited by examiner

FIG. 3
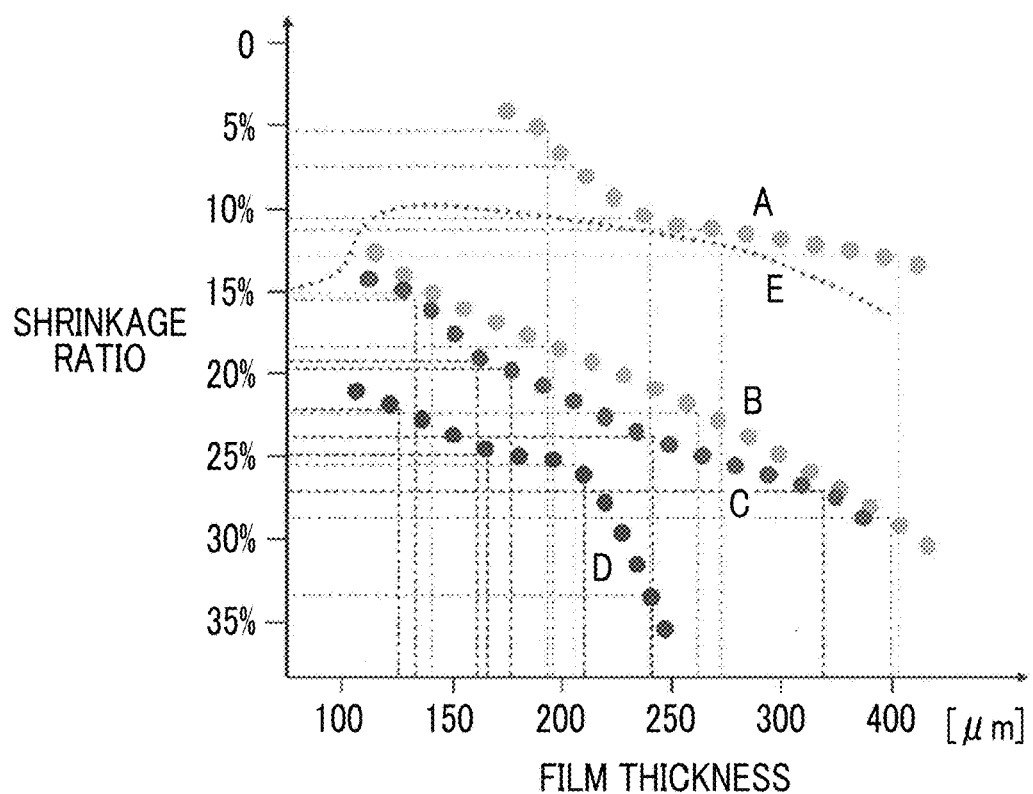
FIG. 4
| WATER ONLY | AQUEOUS ETHANOL SOLUTION |
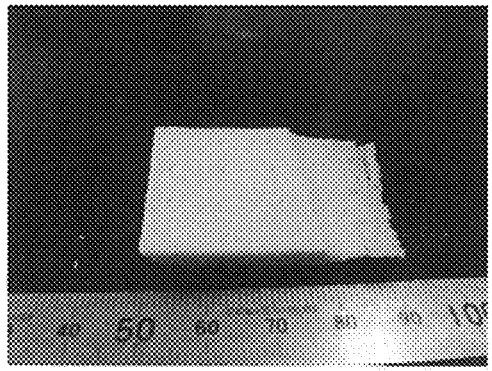 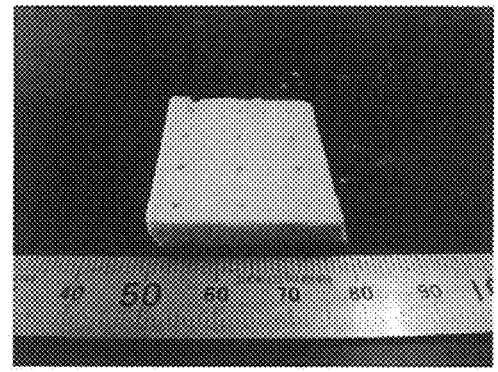
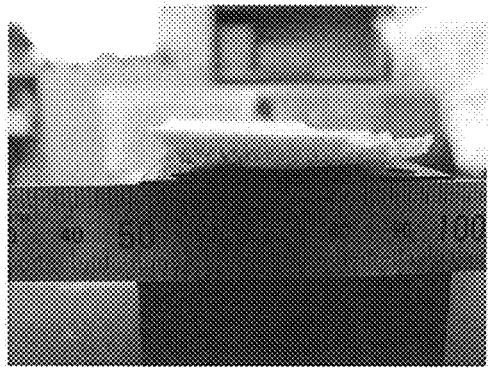 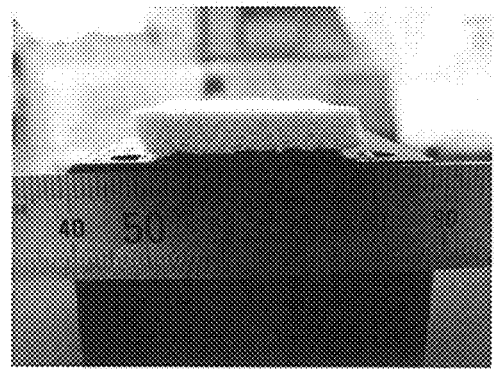

FIG. 5
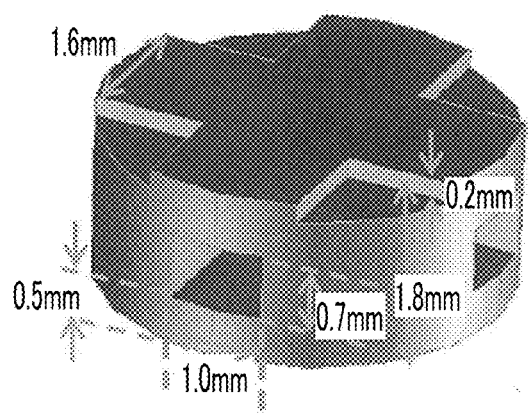
· DISK WITH VOIDS
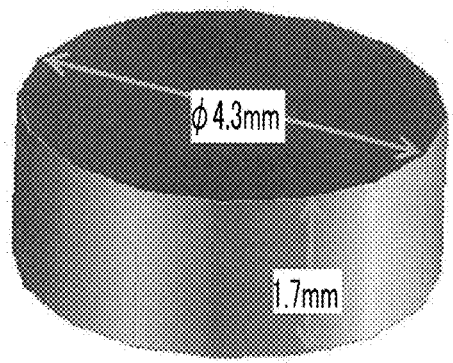
· DISK WITHOUT VOIDS
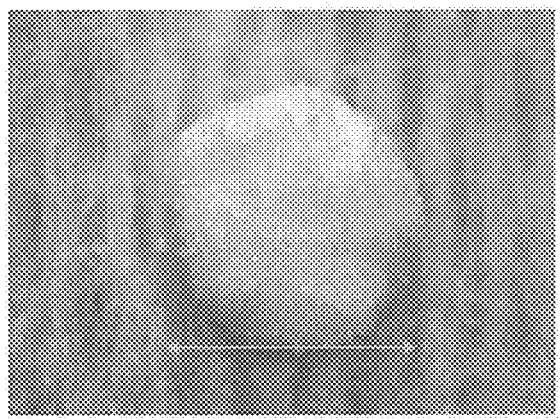
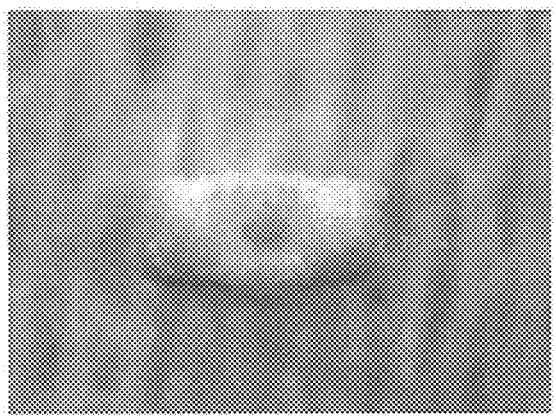

FIG. 6
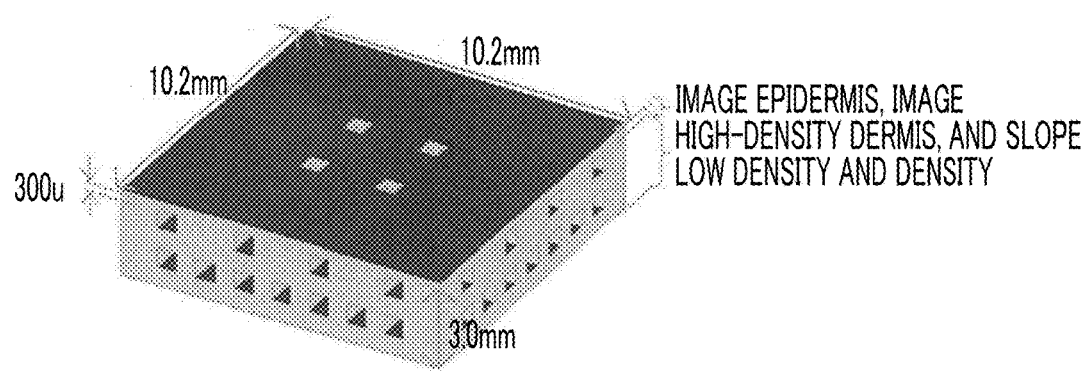
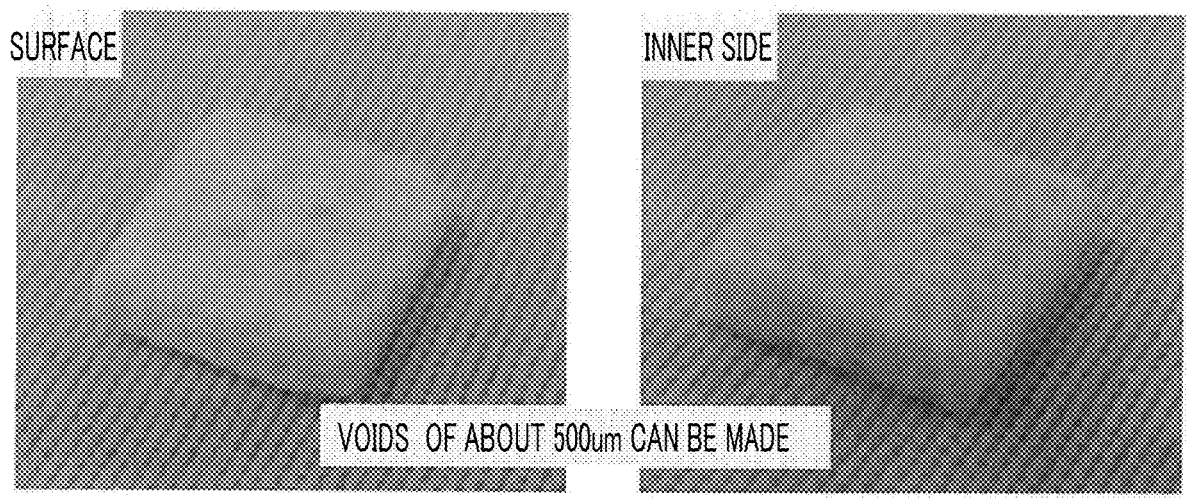

FIG. 9
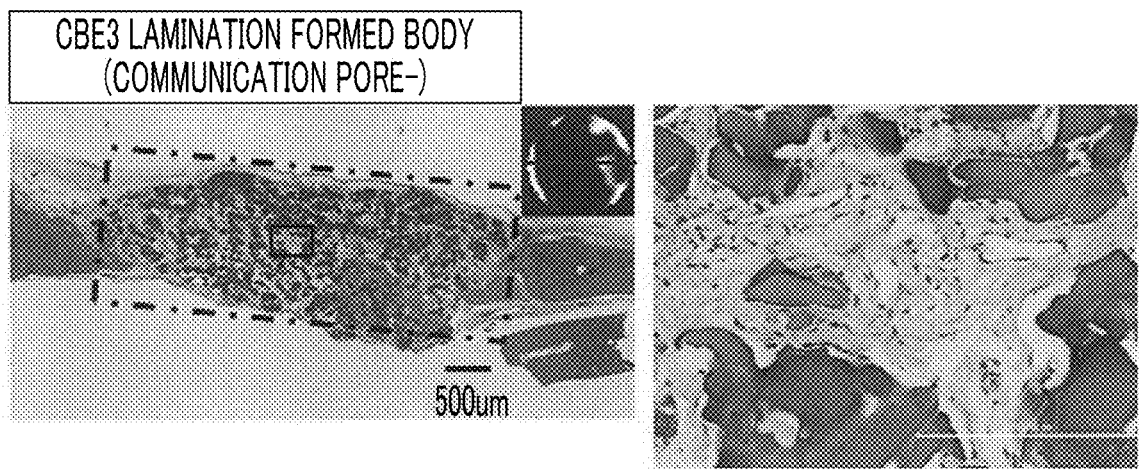
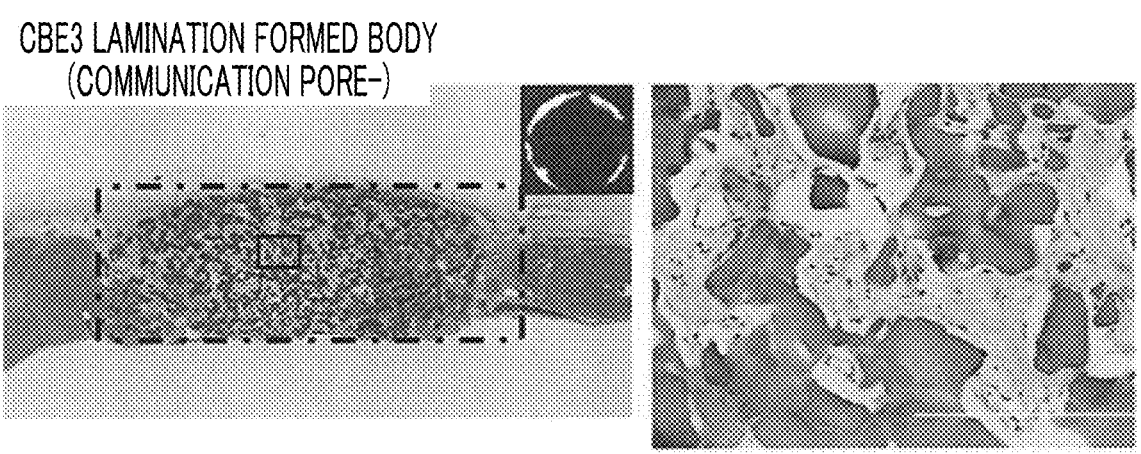

FIG. 10
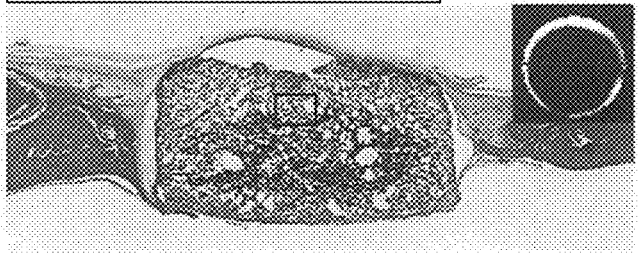
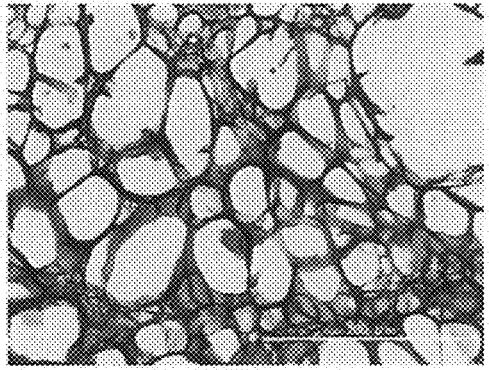
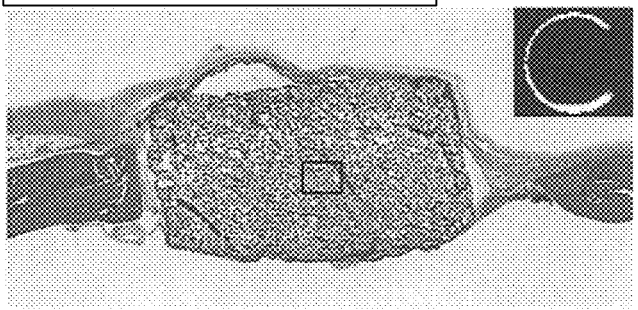
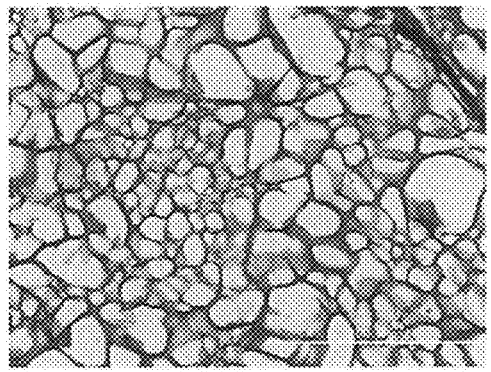

FIG. 13
(2)
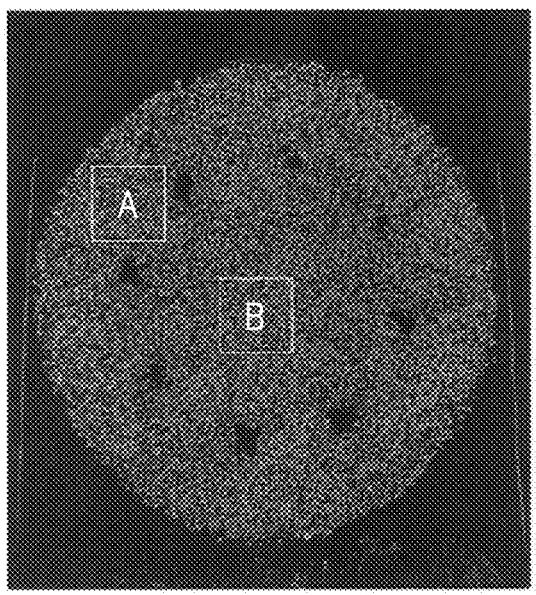
A:70.90%
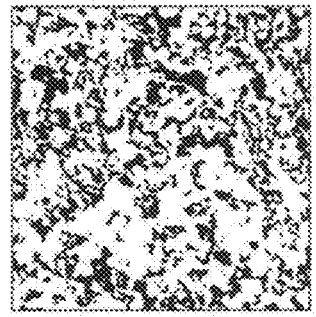
B:70.22%
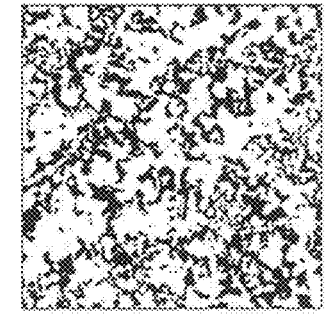
FIG. 14
(3)
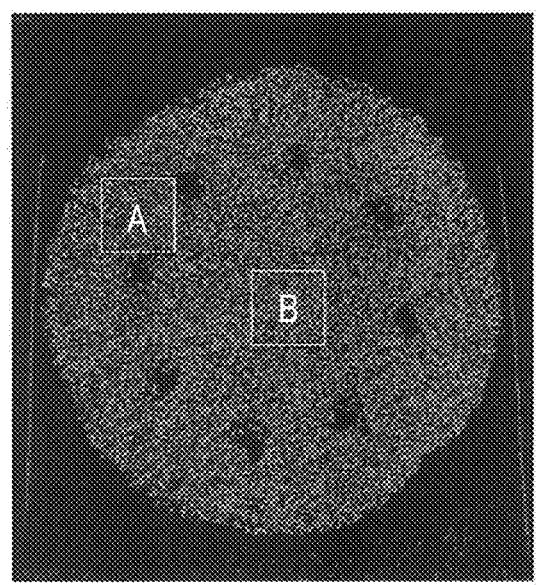
A:64.42%
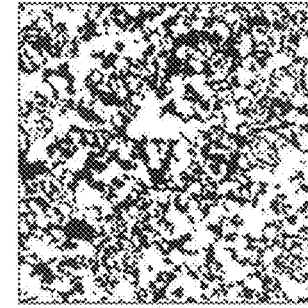
B:65.24%
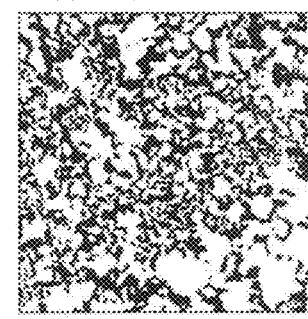

FIG. 15
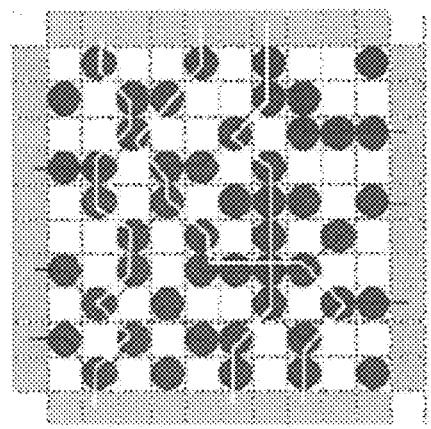
FIG. 16
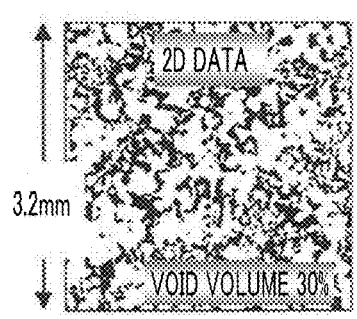 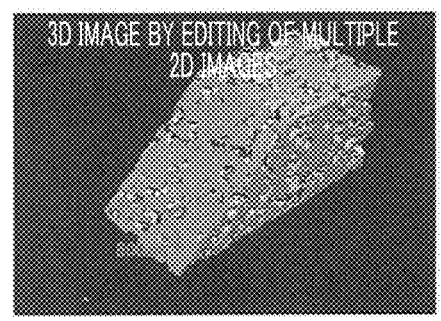 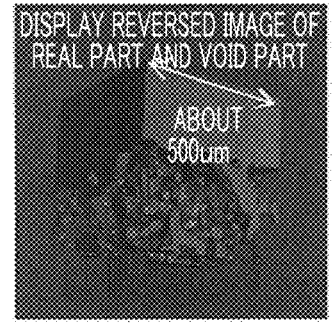

SEQUENCE LISTING

```
<160> NUMBER OF SEQ ID NOS: 10

<210> SEQ ID NO 1
<211> LENGTH: 571
<212> TYPE: PRT
<213> ORGANISM: Artificial Sequence
<220> FEATURE:
<223> OTHER INFORMATION: Synthetic: Recombinant

<400> SEQUENCE: 1

Gly Ala Pro Gly Ala Pro Gly Leu Gln Gly Ala Pro Gly Leu Gln Gly
1               5                   10                  15

Met Pro Gly Glu Arg Gly Ala Ala Gly Leu Pro Gly Pro Lys Gly Glu
            20                  25                  30

Arg Gly Asp Ala Gly Pro Lys Gly Ala Asp Gly Ala Pro Gly Ala Pro
        35                  40                  45

Gly Leu Gln Gly Met Pro Gly Glu Arg Gly Ala Ala Gly Leu Pro Gly
    50                  55                  60

Pro Lys Gly Glu Arg Gly Asp Ala Gly Pro Lys Gly Ala Asp Gly Ala
65                  70                  75                  80

Pro Gly Lys Asp Gly Val Arg Gly Leu Ala Gly Pro Ile Gly Pro Pro
                85                  90                  95

Gly Glu Arg Gly Ala Ala Gly Leu Pro Gly Pro Lys Gly Glu Arg Gly
            100                 105                 110

Asp Ala Gly Pro Lys Gly Ala Asp Gly Ala Pro Gly Lys Asp Gly Val
        115                 120                 125

Arg Gly Leu Ala Gly Pro Ile Gly Pro Pro Gly Pro Ala Gly Ala Pro
```

```
            130                 135                 140
Gly Ala Pro Gly Leu Gln Gly Met Pro Gly Glu Arg Gly Ala Ala Gly
145                 150                 155                 160

Leu Pro Gly Pro Lys Gly Glu Arg Gly Asp Ala Gly Pro Lys Gly Ala
                165                 170                 175

Asp Gly Ala Pro Gly Lys Asp Gly Val Arg Gly Leu Ala Gly Pro Pro
                180                 185                 190

Gly Ala Pro Gly Leu Gln Gly Ala Pro Gly Leu Gln Gly Met Pro Gly
                195                 200                 205

Glu Arg Gly Ala Ala Gly Leu Pro Gly Pro Lys Gly Glu Arg Gly Asp
            210                 215                 220

Ala Gly Pro Lys Gly Ala Asp Gly Ala Pro Gly Ala Pro Gly Leu Gln
225                 230                 235                 240

Gly Met Pro Gly Glu Arg Gly Ala Ala Gly Leu Pro Gly Pro Lys Gly
                245                 250                 255

Glu Arg Gly Asp Ala Gly Pro Lys Gly Ala Asp Gly Ala Pro Gly Lys
                260                 265                 270

Asp Gly Val Arg Gly Leu Ala Gly Pro Ile Gly Pro Pro Gly Glu Arg
                275                 280                 285

Gly Ala Ala Gly Leu Pro Gly Pro Lys Gly Glu Arg Gly Asp Ala Gly
            290                 295                 300

Pro Lys Gly Ala Asp Gly Ala Pro Gly Lys Asp Gly Val Arg Gly Leu
305                 310                 315                 320

Ala Gly Pro Ile Gly Pro Pro Gly Pro Ala Gly Ala Pro Gly Ala Pro
                325                 330                 335

Gly Leu Gln Gly Met Pro Gly Glu Arg Gly Ala Ala Gly Leu Pro Gly
                340                 345                 350

Pro Lys Gly Glu Arg Gly Asp Ala Gly Pro Lys Gly Ala Asp Gly Ala
            355                 360                 365

Pro Gly Lys Asp Gly Val Arg Gly Leu Ala Gly Pro Pro Gly Ala Pro
            370                 375                 380

Gly Leu Gln Gly Ala Pro Gly Leu Gln Gly Met Pro Gly Glu Arg Gly
385                 390                 395                 400

Ala Ala Gly Leu Pro Gly Pro Lys Gly Glu Arg Gly Asp Ala Gly Pro
                405                 410                 415

Lys Gly Ala Asp Gly Ala Pro Gly Ala Pro Gly Leu Gln Gly Met Pro
                420                 425                 430

Gly Glu Arg Gly Ala Ala Gly Leu Pro Gly Pro Lys Gly Glu Arg Gly
            435                 440                 445

Asp Ala Gly Pro Lys Gly Ala Asp Gly Ala Pro Gly Lys Asp Gly Val
            450                 455                 460

Arg Gly Leu Ala Gly Pro Ile Gly Pro Pro Gly Glu Arg Gly Ala Ala
465                 470                 475                 480

Gly Leu Pro Gly Pro Lys Gly Glu Arg Gly Asp Ala Gly Pro Lys Gly
                485                 490                 495

Ala Asp Gly Ala Pro Gly Lys Asp Gly Val Arg Gly Leu Ala Gly Pro
                500                 505                 510

Ile Gly Pro Pro Gly Pro Ala Gly Ala Pro Gly Ala Pro Gly Leu Gln
            515                 520                 525

Gly Met Pro Gly Glu Arg Gly Ala Ala Gly Leu Pro Gly Pro Lys Gly
            530                 535                 540

Glu Arg Gly Asp Ala Gly Pro Lys Gly Ala Asp Gly Ala Pro Gly Lys
545                 550                 555                 560
```

```
Asp Gly Val Arg Gly Leu Ala Gly Pro Pro Gly
            565                 570

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 2

Arg Glu Asp Val
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 3

Tyr Ile Gly Ser Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 4

Pro Asp Ser Gly Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 5

Arg Tyr Val Val Leu Pro Arg
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 6

Leu Gly Thr Ile Pro Gly
1               5

<210> SEQ ID NO 7
<211> LENGTH: 10
<212> TYPE: PRT
<213> ORGANISM: Artificial Sequence
```

```
                                   -continued

<220> FEATURE:
<223> OTHER INFORMATION: Description of Artificial Sequence: adhesive
      sequence

<400> SEQUENCE: 7

Arg Asn Ile Ala Glu Ile Ile Lys Asp Ile
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 8

Ile Lys Val Ala Val
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 9

Asp Gly Glu Ala
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: adhesive
      sequence

<400> SEQUENCE: 10

Glu Arg Gly Asp
1
```

METHOD FOR PRODUCING GELATIN FORMED BODY AND GELATIN FORMED BODY

CROSS-REFERENCE TO RELATED APPLICATIONS

This application is a Continuation of PCT International Application No. PCT/JP2017/021124 filed on Jun. 7, 2017, which claims priority under 35 U.S.C § 119(a) to Japanese Patent Application No. 2016-114252 filed on Jun. 8, 2016 and Japanese Patent Application No. 2017-030322 filed on Feb. 21, 2017. Each of the above application(s) is hereby expressly incorporated by reference, in its entirety, into the present application.

REFERENCE TO SEQUENCE LISTING SUBMITTED VIA EFS-WEB

This application includes an electronically submitted sequence listing in .txt format. The .txt file contains a sequence listing entitled "2019-02-11 2870-0710PUS1 ST25.txt" created on Feb. 11, 2019 and is 7,187 bytes in size. The sequence listing contained in this .txt file is part of the specification and is hereby incorporated by reference herein in its entirety.

BACKGROUND OF THE INVENTION

1. Field of the Invention

The present invention relates to a method for producing a gelatin formed body by jetting liquid droplets of a predetermined aqueous alcohol solution from a nozzle and causing the jetted liquid droplets to fly and land on a layer containing a gelatin powder. The present invention further relates to a gelatin formed body produced by the method.

2. Description of the Related Art

The practical use of regenerative medicine for regenerating living tissues or organs that have been impaired by dysfunction or malfunction has been promoted. Regenerative medicine is a medical technology that uses one or more of a cell, a scaffold, and a growth factor to regenerate the same form and function as those of the original tissue, in living tissues that cannot be recovered by the natural healing ability of the living body alone. In regenerative medicine, a three-dimensional formed body constructed using gelatin or the like is used in some cases.

JP2009-102526A discloses a three-dimensional shaping material including a binder and a powder material, in which the binder contains a polymerizable compound having at least one polymerizable group, and one of the powder material or the polymerizable compound has a cationic group and/or a group capable of serving as a cationic group and the other has an organic acid residue and/or a salt thereof. JP2010-228316A discloses a method for producing a three-dimensional shaped article having a surface layer, including (i) a layer forming step of forming a powder material into a layer having a predetermined thickness on a support, (ii) a bonding step of bonding the powder material in the above layer with a binder so as to have a cross-sectional shape obtained by cutting an object to be shaped in parallel cross sections, (iii) a construction step of sequentially repeating the steps (i) and (ii) to construct a three-dimensional shaped article, (iv) a coating step of coating the surface of the constructed three-dimensional shaped article with a photocurable composition containing (1) an ethylenically unsaturated compound and (2) a photopolymerization initiator, and (v) a curing step of photocuring the coated photocurable composition. JP2010-228103A discloses a three-dimensional shaping material including a powder material and a binder, in which the binder contains a polymer having a monomer unit having a heteroaromatic ring group.

JP2016-037041A discloses a three-dimensional shaping powder material including particles in which a plurality of core materials are immobilized by a water-soluble resin, as a powder material used for three-dimensional shaping in which a plurality of powder material layers having a predetermined shape bonded by a resin are laminated to shape a three-dimensional object. In addition, JP2016-055531A discloses a method for producing a three-dimensional shaped article of laminating layers to produce the three-dimensional shaped article, including a layer forming step of thinking a layer using a three-dimensional shaping composition including particles having isocyanate groups on the surface thereof, a water-soluble resin having a hydroxyl group, and an aqueous solvent, and an ink jetting step of jetting a curable ink to the layer.

SUMMARY OF THE INVENTION

There are reports on the production of a three-dimensional formed body using a gypsum powder or starch powder as in the Z printer series of Z Corporation and three-dimensional printing using organic materials as described in the foregoing patent documents. However, it is desired to develop a method of producing a gelatin formed body for use in regenerative medicine, particularly a gelatin formed body having high biocompatibility and high shaping accuracy due to no incorporation of a harmful component which inhibits biocompatibility.

An object of the present invention is to provide a method for producing a gelatin formed body having a minimized content of a component harmful to a living body and high biocompatibility with high shaping accuracy, and a gelatin formed body produced by the method.

As a result of extensive studies to achieve the foregoing object, the present inventors have found that a gelatin formed body having high biocompatibility can be produced with high shaping accuracy by forming, on a substrate, a layer containing a powder which is obtained by air-drying an aqueous gelatin solution and has an average particle diameter of 25 to 200 µm, and then jetting liquid droplets of an aqueous solution containing alcohols having a boiling point of 120° C. or lower from a nozzle and flying the jetted liquid droplets so that the liquid droplets are landed on the layer. The present invention has been completed based on these findings.

That is, according to the present invention, the following inventions are provided.

(1) A method for producing a gelatin formed body, the method comprising: a step a of forming, on a substrate, a layer containing a powder which is obtained by air-drying an aqueous gelatin solution and has an average particle diameter of 25 to 200 µm; and a step b of jetting liquid droplets of an aqueous solution containing alcohols having a boiling point of 120° C. or lower toward the layer formed in the step a from a nozzle and flying the jetted liquid droplets so that the liquid droplets are landed on the layer formed in the step a, thereby forming a gelatin formed body.

(2) The method for producing a gelatin formed body according to (1), in which the gelatin in the step a is animal gelatin or recombinant gelatin.

(3) The method for producing a gelatin formed body according to (1) or (2), in which the alcohol having a boiling point of 120° C. or lower in the step b is ethanol.

(4) The method for producing a gelatin formed body according to any one of (1) to (3), further comprising: after the step b, a step c of forming a layer containing a powder which is obtained by air-drying an aqueous gelatin solution and has an average particle diameter of 25 to 200 μm on the layer formed in the step a and the gelatin formed body formed in the step b; and a step d of jetting liquid droplets of an aqueous solution containing alcohols having a boiling point of 120° C. or lower from a nozzle and flying the jetted liquid droplets so that the liquid droplets are landed on the layer formed in the step c, thereby producing a gelatin formed body.

(5) The method for producing a gelatin formed body according to (4), in which the gelatin in the step c is animal gelatin or recombinant gelatin.

(6) The method for producing a gelatin formed body according to (4) or (5), in which the alcohol having a boiling point of 120° C. or lower in the step d is ethanol.

(7) The method for producing a gelatin formed body according to any one of (1) to (6), in which in the step b, the produced gelatin formed body is in contact with the substrate.

(8) The method for producing a gelatin formed body according to any one of (1) to (3), further comprising: after the step b, a step c1 of forming a layer containing a powder which is obtained by air-drying an aqueous gelatin solution and has an average particle diameter of 25 to 200 μm on the layer formed in the step a and the gelatin formed body formed in the step b; and a step d1 of jetting liquid droplets of an aqueous solution containing alcohols having a boiling point of 120° C. or lower from a nozzle and flying the jetted liquid droplets so that the liquid droplets are landed on the layer formed in the step c1, thereby producing a gelatin formed body; and further comprising, after the step d1, a step e of forming a layer containing a powder which is obtained by air-drying an aqueous gelatin solution and has an average particle diameter of 25 to 200 μm on the layer formed in the step c1 and the gelatin formed body formed in the step d1; and a step f of jetting liquid droplets of an aqueous solution containing alcohols having a boiling point of 120° C. or lower from a nozzle and flying the jetted liquid droplets so that the liquid droplets are landed on the layer formed in the step e, thereby producing a gelatin formed body, in which, in the step b, the produced gelatin formed body is in contact with the substrate, in the step d1, the liquid droplets are landed on a region corresponding to the outer peripheral region of the upper surface of the gelatin formed body formed in the step b, and in the step f, the liquid droplets are landed in a region corresponding to the outer peripheral region of the upper surface of the gelatin formed body formed in the step d1 and in a region inside the region surrounded by the gelatin fanned body formed in the step d1.

(9) The method for producing a gelatin formed body according to any one of (1) to (8), further comprising a step g of removing the powder not used for forming a gelatin formed body.

(10) The method for producing a gelatin formed body according to (9), further comprising a step h of heating the formed body to cure the formed body, after the step g.

(11) The method for producing a gelatin formed body according to (10), in which the formed body is heated for 1 hour to 72 hours.

(12) The method for producing a gelatin formed body according to any one of (1) to (11), further comprising a step i of encapsulating the gelatin formed body with a support.

(13) The method for producing a gelatin formed body according to any one of (1) to (12), further comprising a step j of seeding the cells into the gelatin formed body.

(14) The method for producing a gelatin formed body according to any one of (1) to (13), in which the gelatin formed body is a scaffold for regenerative medicine or a tissue repair material.

(15) A gelatin formed body produced by the method for producing a gelatin formed body according to any one of (1) to (14).

(16) The gelatin formed body according to (15), which is a scaffold for regenerative medicine or a tissue repair material.

(17) The gelatin formed body according to (15) or (16), which is a tissue repair material for bone regeneration.

(18) The gelatin formed body according to any one of (15) to (17), in which the void volume is 20% to 40%.

(19) The gelatin formed body according to any one of (15) to (18), which has a pore communicating with an external space.

(20) The gelatin formed body according to (19), in which the pore communicating with an external space passes through the inside of the formed body and communicates with the external space at both ends of the pore.

(21) The gelatin formed body according to (19) or (20), in which a representative diameter of the pore communicating with the external space is 300 μm to 2000 μm.

(22) The gelatin formed body according to any one of (15) to (21), in which the surface is encapsulated with a support.

According to the method for producing a gelatin formed body according to the present invention, it is possible to produce a gelatin formed body having a minimized content of a component harmful to a living body and high biocompatibility with high shaping accuracy. The gelatin formed body of the present invention has high biocompatibility and high shaping accuracy.

BRIEF DESCRIPTION OF THE DRAWINGS

FIG. 3 shows the results of evaluating the relationship between the average particle diameter and aqueous solution composition of the powder and the film thickness and shrinkage ratio.

FIG. 4 shows a gelatin formed body produced using water or an aqueous ethanol solution as a jetting liquid.

FIG. 5 shows a 3D (three-dimensional) design drawing of a formed body having voids and a formed body not having voids, and a formed body having voids produced.

FIG. 6 shows a 3D (three-dimensional) design drawing of a formed body having voids and a formed body having voids produced.

FIG. 9 shows the results of pathological analysis for evaluation of bone regeneration (formed article without communication pores).

FIG. 10 shows the results of pathological analysis for evaluation of bone regeneration (freeze-dried sponge).

FIG. 13 shows the measurement results of the filling rate of the gelatin formed body.

FIG. 14 shows the measurement results of the filling rate of the gelatin formed body.

FIG. 15 is a diagram showing that a path is generated both in the vertical direction and the horizontal direction in the case where the dot serving as the path is 50% in two dimensions.

FIG. 16 is a diagram showing that, according to micro-CT analysis, a formed body obtained by laminating gelatin powders has a communication pore structure having a void volume of 30% in which pores having a diameter of about 100 μm are three-dimensionally connected to one another.

DESCRIPTION OF THE PREFERRED EMBODIMENTS

Figure 1:
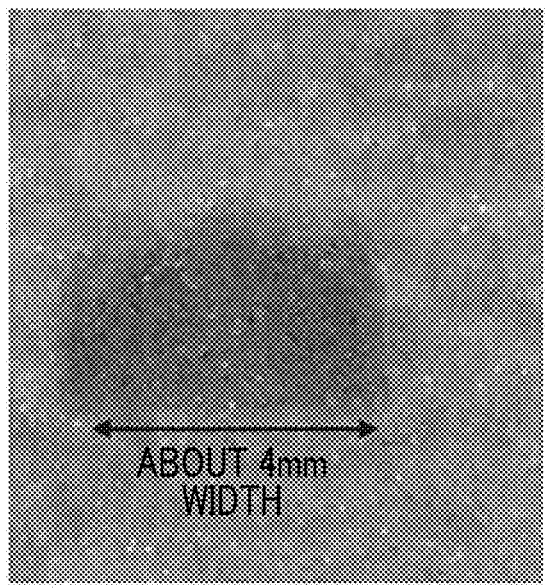
FIG. 1 shows a formed body produced using air-dried gelatin powder.

Hereinafter, an embodiment of the present invention will be described in detail.

[1] Method for Producing Gelatin Formed Body

The method for producing a gelatin formed body according to the embodiment of the present invention includes a step a of forming, on a substrate, a layer containing a powder which is obtained by air-drying an aqueous gelatin solution and has an average particle diameter of 25 to 200 μm; and a step b of jetting liquid droplets of an aqueous solution containing alcohols having a boiling point of 120° C. or lower toward the layer formed in the step a from a nozzle and flying the jetted liquid droplets so that the liquid droplets are landed on the layer formed in the step a, thereby forming a gelatin formed body.

In the present invention, by using a powder having an average particle diameter of 25 to 200 μm after air-drying the aqueous gelatin solution, and by using an aqueous solution containing alcohols having a boiling point of 120° C. or lower, a high-accuracy gelatin formed body with virtually no warpage or shrinkage and with the upper and lower layers being firmly bonded to each other can be produced with high shaping accuracy.

<1> Powder which is Obtained by Air-Drying Aqueous Gelatin Solution and has Average Particle Diameter of 25 to 200 μm The powder used in the present invention is a powder obtained by air-drying an aqueous gelatin solution or a powder obtained by processing a solid obtained by air-drying the aqueous gelatin solution.

The air-drying described in the present specification is a process for drying at a temperature of 0° C. or higher and 60° C. or lower and is carried out at atmospheric pressure or under reduced pressure. Since the gelatin has a different molecular structure after drying depending on the drying temperature, the swelling properties of the powder can be adjusted by changing the drying temperature. In the case where the drying temperature is too high, it is not preferable because the size changes due to swelling during ink jet drawing become large. On the other hand, in the case where the drying temperature is too low, the dissolution rate will be slower, which is thus not preferable from the viewpoint of the production efficiency of the shaping by lamination. Therefore, the drying temperature is preferably 10° C. to 40° C. and more preferably 20° C. to 30° C. In order to promote drying, a method such as depressurization or blowing can be used in combination. The pressure is preferably in the range of 1 atm to the water vapor pressure at each temperature.

In the case where a powder is produced by freeze-drying the aqueous gelatin solution instead of air-drying the aqueous gelatin solution, the powder is dissolved in the ink and therefore cannot be shaped in the case where an aqueous alcohol solution is ink jet drawn into the freeze-dried powder. It is considered due to the fact that, in the case of freeze-drying, one powder particle is in a state in which a large number of holes are opened, and has a small density so that the powder is easily dissolved in the aqueous alcohol solution. Since the powder which is obtained by air-drying an aqueous gelatin solution and has an average particle diameter of 25 to 200 μm has almost no voids on the surface of the particle, the specific surface area of the particle is small and even in the case of drawing by ink jet, only some of the powder particles and the surfaces of the powder particles are dissolved.

The average particle diameter of the powder used in the present invention is 25 to 200 μm. In the case where the average particle diameter is less than 25 μm or the average particle diameter is more than 200 μm, a desired three-dimensional powder laminate (formed body) cannot be formed.

(Method for Measuring Average Particle Diameter of Powder)

The average particle diameter of the powder used in the present invention can be measured by a generally known method. Specifically, the average particle diameter of the powder can be measured using a direct observation method (optical microscope or electron microscope), a laser diffraction/light scattering method, a centrifugal sedimentation method, an electrical sensing zone method, a photon correlation method, or the like. As a measurement method, there are a dry method in which the measurement is carried out in air or another gas at the time of measurement, and a wet method in which particles are dispersed in an appropriate solvent, followed by measurement. The direct observation method can be carried out by measurement with a dry method; the laser diffraction/light scattering method can be carried out by measurement with a dry method or a wet method; and the centrifugal sedimentation method, the electrical sensing zone method, and the photon correlation method can be carried out by measurement with a wet method.

Among the above measurement methods, the wet laser diffraction/light scattering method is excellent in accuracy, reproducibility, and convenience in measurement. The particle size distribution analyzer using the wet laser diffraction/light scattering method is commercially available. Examples of commercially available particle size distribution analyzers include a laser diffraction particle size distribution analyzer SALD (available from Shimadzu Corporation), MASTERSIZER (available from Malvern Panalytical Inc.), a MICROTRAC MT (available from MicrotracBEL Corp.), a laser diffraction/light scattering particle size distribution analyzer LS 13 (available from Beckman Coulter, Inc.), a LASER MICRON SIZER (available from Seishin Enterprise Co., Ltd.), and a laser diffraction/light scattering type particle size distribution analyzer LA series (available from Horiba Corporation). In the Examples of the present invention, a laser diffraction/light scattering particle size distribution analyzer LA920 (available from Horiba Corporation) was used mainly.

As a solvent for use in the wet particle size distribution measurement, it is necessary to select a solvent other than a solvent that dissolves gelatin or a solvent that swells gelatin. Examples of the suitable solvent that can be used include alcohols, ketones, esters, hydrocarbons, and silicone oils, but alcohols are preferable for reasons such as safety and refractive index, among which ethanol and isopropanol are particularly preferable. The measurement temperature is 25° C.(±3° C.) unless otherwise noted.

The particle diameter measured by the wet laser diffraction/light scattering method is expressed in the form of a particle size distribution converted into a sphere equivalent diameter. The average particle diameter in the present invention represents a median diameter (50% diameter) unless otherwise specified. Besides the median diameter, the 10% diameter and the 90% diameter are sometimes used for the characteristics of particles, but these diameters are all determined from the particle size distribution measured by the wet laser diffraction/light scattering method.

(About Upper Limit and Lower Limit of Average Particle Diameter of Powder)

In the case where the average particle diameter of the powder is larger than 200 μm, the minimum unit of the powder laminate (formed body) also becomes 200 μm in all the X, Y and Z directions, making it impossible to construct a high-accuracy formed body. In addition, in the case of powder lamination as in the present invention, there is a lower limit for the average particle diameter of the powder mainly due to the following two reasons (Reason 1 and Reason 2).

Reason 1: Poor Recoating Due to Deteriorated Fluidity and Increased Aggregating Properties of Powder It is generally known that, in the case where the average particle diameter is made smaller, the fluidity of the powder which is an aggregate of particles tends to deteriorate or agglomerates tend to occur. In the case where the average particle diameter becomes smaller and therefore the fluidity deteriorates and agglomerates occur, the recoating becomes difficult. Also in connection with fish gelatin, in the case where the average particle diameter is 21 μm, the powder adheres to the roller, and unevenness that can be visually observed occurred on a part of the recoating surface, so that high-accuracy recoating could not be carried out.

Reason 2: High-Accuracy Structure is Constructed by Achieving both Increased Film Thickness and Suppressed Film Stress As an example of an embodiment of the present invention, it is assumed that, after flattening gelatin powder, which is an aggregate of powder particles, using a roller or blade or the like, a planar coated surface is formed by scanning an ink jet head or the like in the XY direction which is horizontal to the powder, while the jetting liquid is jetted from an ink jet head or the like to cause the jetting liquid to fly from the top to the bottom of the powder so that the jetting liquid is landed on the surface of the powder. In this case, the jetting liquid that has landed enters the gaps between the particles which are constituent elements of the powder and the particles, the jetting liquid is positioned between the two or more adjacent particles, the surface of the particles of the powder is dissolved by the jetting liquid, and then drying of the jetting liquid progresses, so that the particles of the powder temporarily adhere to one another. In the case of the powder lamination forming the film of one layer in the above system, the following tendency is observed.

Here, the surface of the powder is not the surface of every one of the powder particles constituting the powder but the side of the air layer on the upper part of the powder which is an aggregate of the particles. Here, the surface of the particle is the surface of the particle which is a constituent element of the powder.

In the case where drawing is carried out with increasing the liquid droplet volume deposited per unit area, the amount of jetting liquid permeating from the surface of the powder to the inside thereof increases and the film thickness becomes larger, but the film stress (shrinkage and warpage of the film) increases. In the case where the liquid droplet volume deposited per unit area is reduced, the film stress is small but the film thickness becomes smaller. In the powder lamination, since there is a lower limit on the lamination pitch in the Z direction, the film thickness is required to be equal to or greater than a certain value.

There is a lower limit on the lamination pitch in the Z direction due to the following two reasons.

Reason 2-1: Suppression of Increase in Shaping Time of Powder Lamination

In the case where the lamination pitch in the Z direction is set to a small value, the number of lamination times increases in order to obtain a desired thickness and therefore the shaping speed of the three-dimensional object becomes slower. More accuracy than necessary is unnecessary for shaping speed.

Reason 2-2: Mechanical Accuracy

Requirement from mechanical accuracy for scanning with no fluctuation while maintaining the horizontal level in recoating In the present powder lamination, the lamination pitch for one layer is about 100 μm.

It is necessary to obtain a film thickness of about 150 μm to 200 μm as the film thickness required for forming one layer, in consideration of the fact that the lamination pitch for one layer is 100 μm, and the upper and lower layers are closely attached to each other.

It is important to obtain a predetermined film thickness in the case of producing a formed body by powder lamination.

However, in the case where the liquid droplet volume deposited per unit volume is increased in order to obtain a predetermined film thickness, it is not possible to obtain an appropriate structure due to the film stress. In the case where the liquid droplet volume deposited per unit volume is made small in order to lower the film stress, the upper and lower films are not closely attached to each other and therefore a three-dimensional structure cannot be obtained.

The relationship between increasing the film thickness and suppressing the film stress with increase and decrease of the liquid droplet volume deposited per unit volume as a design matter is a trade-off, which is an obstacle to forming a powder laminate like the present invention.

However, as described above, even in the case where the relationship between increasing the film thickness and suppressing the film stress with increase and decrease of the liquid droplet volume deposited per unit volume as a design matter is a trade-off, the trade-off relationship is resolved rather than passive things such as adjustment of the trade-off relationship, thus making it possible to make the film thickness large and suppress film stress, in the case where the average particle diameter of the powder is increased.

Further, the degree of compatibility increases depending on the size of the average particle diameter of the powder.

The coating amount per unit area can be controlled by adjusting the amount of one liquid droplet jetted from one nozzle or adjusting the distance between the liquid droplets to be landed and the landing density.

(As to Method of Preparing Powder)

The powder having an average particle diameter of 25 to 200 μm can be prepared, for example, by pulverizing a solid obtained by air-drying gelatin.

The air-dried gelatin solid can be pulverized using a known mechanical pulverizer. As the pulverization method, there are a dry pulverization method and a wet pulverization method, but in the case of the present invention, a dry pulverization method is preferable. Representative examples of the dry pulverizer include a high-speed rotary impact mill, a roller mill, a jet mill, and a medium agitating mill.

The high-speed rotary impact mill is used for pulverizing by impacting a solid mass with a high-speed rotating hammer, pin, disk, or the like. Various devices are commercially available depending on the average particle diameter before and after pulverization. For example, a jaw crusher, a hammer mill, or the like is used in the case where the average particle diameter after pulverization is cm level, and a rod mill, a pin mill, or the like is used in the case where the average particle diameter after pulverization is at the level of several millimeters. In the case where the average particle diameter after pulverization is at the level of several tens of micrometers, a mill comprising a higher speed stirring disk or impeller is used. In addition, by comprising a high-speed rotating body and a screen on the outer periphery thereof, it is preferable to use a device which improves the uniformity of the pulverized particles by exhibiting the miniaturization by the shearing force and the partial classification function.

In the roller mill, a solid to be pulverized is put between rotating rollers, and the solid is crushed and pulverized by the pressure between the rollers. A roll crusher is one by which the average particle diameter after pulverization is at the level of several centimeters, and a roller mill is one by which the average particle diameter after pulverization is at the level of several millimeters.

The jet mill carries out miniaturization of particles by particle-particle collision or collision of particles against walls or the like, or grinding of particles due to high-speed airflow and is suitable mainly for producing fine particles of 10 μm or less. One type of this method is a method of pulverizing particles by blowing a high-speed airflow against a dedicated collision plate, rather than particle-particle collision. A device called collision type jet mill is also commercially available, and this collision type jet mill is also suitable for pulverizing particles of gelatin having a small specific gravity.

A typical example of the medium agitating mill is a ball mill. The ball mill carries out miniaturization of particles by impact, compression, and grinding by means of metal, magnetic, or metal oxide balls, in which miniaturization is done by putting a sample and balls in a single pot, followed by rotation for a long period of time. However, there is also a ball mill that pulverizes a sample by subjecting to vibration at a high frequency instead of rotation.

It is possible to use the above-described pulverization method for pulverizing the air-dried gelatin solid, but in particular, it is important that the temperature during pulverization does not become too high in the case of pulverizing gelatin. It is desirable to maintain the temperature of the particles during pulverization at 80° C. or lower, preferably 60° C. or lower. Therefore, it is preferred that the pulverizer comprises a cooling mechanism such as air cooling or water cooling. It is also effective to positively freeze and then pulverize using liquid nitrogen or the like. In addition, in order to achieve the pulverization efficiency and to narrow the average particle size distribution of the produced particles, it is preferable to comprise a classification mechanism in the pulverizer. For the classification mechanism, screen or centrifugal separation is common. Furthermore, in view of the performance of the pulverizer, it is difficult to pulverize the air-dried gelatin solid to a level of several tens of micrometers by a single operation. Generally, by using several pulverizers corresponding to the pulverization level in stages, it is possible to obtain a fine powder having a uniform average particle diameter.

<2> Step a of Forming Layer Containing Air-Dried Powder of Aqueous Gelatin Solution on Substrate The step a in the present invention is a step of forming a layer containing a powder having an average particle diameter of 25 to 200 μm, which is obtained by air-drying an aqueous gelatin solution, (also referred to as a gelatin powder), on a substrate. The substrate may be provided on the lifting stage.

The material, shape, and size of the substrate are not particularly limited, and an appropriate substrate can be used depending on the purpose. The substrate is preferably a substrate having a plane of a predetermined area. The size of the surface of the substrate is not particularly limited, but it is preferably about 0.5 cm×0.5 cm to 50 cm×50 cm, and more preferably about 3 cm×3 cm to 15 cm×15 cm. The shape of the surface of the substrate may be a square or a rectangle.

Examples of the material for the substrate include metal materials such as stainless steel, aluminum, copper, and iron, inorganic materials such as glass and ceramics, and plastic materials such as acryl, methacryl (such as polymethyl methacrylate resin), polystyrene, polypropylene, and Teflon (registered trademark).

The step of forming the layer containing the gelatin powder on the substrate can be carried out by any method which is not particularly limited, but for example, a 3D printer (three-dimensional printer) can be used. Z-Printer 310 Plus (available from 3D Systems Corporation (formerly Z Corporation)) or the like can be used as an example of the 3D printer, which is not particularly limited.

<3> Aqueous Solution Containing Alcohols

In the present invention, an aqueous solution containing alcohols having a boiling point of 120° C. or lower is used.

The reasons why water is used as a jetting liquid for forming a formed body are as follows.

Reason 1-1: The body is rich in water, and water is basically harmless and highly safe.

Reason 1-2: The gelatin powder can be dissolved and the powder particles can temporarily adhere to one another.

The formed body of the gelatin powder of the present invention can be shaped by powder lamination. As an example of shaping by powder lamination, as described above in the present specification, a planar coated surface is formed by scanning an ink jet head or the like in the XY direction which is horizontal to the powder, while, after flattening a gelatin powder, which is an aggregate of powder particles, using a roller, a blade, or the like, a jetting liquid of about 1 pL to 1000 pL and more favorably 10 pL to 100 pL is jetted from an ink jet head or the like having 1 nozzle to 3,000 nozzles and more favorably 100 nozzles to 3,000 nozzles to cause the jetting liquid to fly from the top to the bottom of the surface of the powder about 0.5 mm to 5 mm and more favorably about 2 mm to 3 mm, so that the jetting liquid is landed on the surface of the powder at 0.5 kHz to 50 kHz and more favorably 3 kHz to 20 kHz. In this case, the jetting liquid that has landed enters the gaps between the particles which are constituent elements of the powder and the particles, the jetting liquid is positioned between the two or more adjacent particles, the surface of the particles of the powder is dissolved by the jetting liquid, and then drying of the jetting liquid progresses, so that the particles of the powder temporarily adhere to one another. Besides the ink jet head, a jet dispenser or the like is also conceivable. In the case of a jet dispenser, it is usually provided with one nozzle.

The water dissolves gelatin and a small amount of water is easily dried. In the case where microliquid droplets (about 2 pL to 300 pL) such as ink jet are uniformly applied to the powder in a planar form, it is easily dried almost even at room temperature within about 10 minutes after powder formation. However, since water has the following problems, an aqueous solution containing alcohols is used in the present invention. The reasons for using an aqueous solution containing alcohols are as follows.

(Reason for Using Aqueous Solution Containing Alcohols)

Reason 2-1: High-accuracy structure is constructed by achieving both increased film thickness and suppressed film stress.

In the case where the surface of the particles of the powder is dissolved by the jetting liquid and drying of the jetting liquid progresses, in a system in which particles of the powder temporarily adhere to one another, in the case where a single layer film is formed by drawing with ink jet, increasing the liquid droplet volume deposited per unit volume as a design matter, in order to increase the film thickness, increases the film stress (shrinkage and warpage of the film), and on the contrary, decreasing the liquid droplet volume deposited per unit volume as a design matter, in order to suppress the occurrence of film stress, decreases the film thickness.

The relationship between increasing the film thickness and suppressing the film stress with increase and decrease of the liquid droplet volume deposited per unit volume as a design matter is a trade-off, which is an obstacle to forming a high-accuracy powder laminate. However, as described above, even in the case where the relationship between increasing the film thickness and suppressing the film stress with increase and decrease of the liquid droplet volume deposited per unit volume as a design matter is a trade-off, the trade-off relationship is eliminated, thus making it possible to make the film thickness large and suppress film stress, in the case where an aqueous solution containing alcohols is used (see FIG. 3).

This is presumed to be the following mechanism.

Although particles of the gelatin powder are dissolved in water, it is assumed that the outermost surface of the particles of gelatin powder is highly likely to be hydrophobic rather than hydrophilic. Therefore, in a mixed solution of water and alcohols, the liquid permeates deep into the powder due to an effect of lowered surface tension of the jetting liquid and an effect of being easily wetted on the surface of the particles resulting from the increased compatibility between the hydrophobic surface and the aqueous alcohol solution. Easy permeation into the powder makes it possible to obtain a powder laminate having the same film thickness as that of water even in the case where the liquid droplet volume deposited per unit area is small. In the case where the surface of the particles of the powder is dissolved by the jetting liquid and then the jetting liquid is evaporated and dried, the particles of the powder temporarily adhere to one another by the gelatin component. In the case where the liquid is positioned between the particles, it becomes a liquid crosslinked state and therefore an attracting force is generated between the particles, which results in shrinkage of the film body of the powder. In the case where an aqueous solution containing alcohols is used, the amount of jetting liquid positioned between the particles is small since the same film thickness is obtained with a small liquid droplet volume deposited per area, and the shrinkage of the film of the powder is reduced since the force for attracting the particles to the particles is weak.

The reason why the outermost surface of the gelatin particles is assumed not to be hydrophilic is that, in the case where moisture evaporates from the aqueous gelatin solution during the drying process of granulation of gelatin powder, gelatin molecules, or hydrophilic groups in the gelatin molecules face each other and the hydrophobic groups are opposite to each other, thus resulting in stabilization, and that the hydrophilic groups oriented toward the outside of the outermost surface are reduced, thus becoming relatively hydrophobic. Even in the case where a large piece of solid gelatin constructed from an aqueous gelatin solution is pulverized, the solid gelatin is separated from a hydrophobic surface having a weak binding force and becomes two or more fine particles, and therefore the outermost surface of the particle is believed to be hydrophobic.

Figure 20:
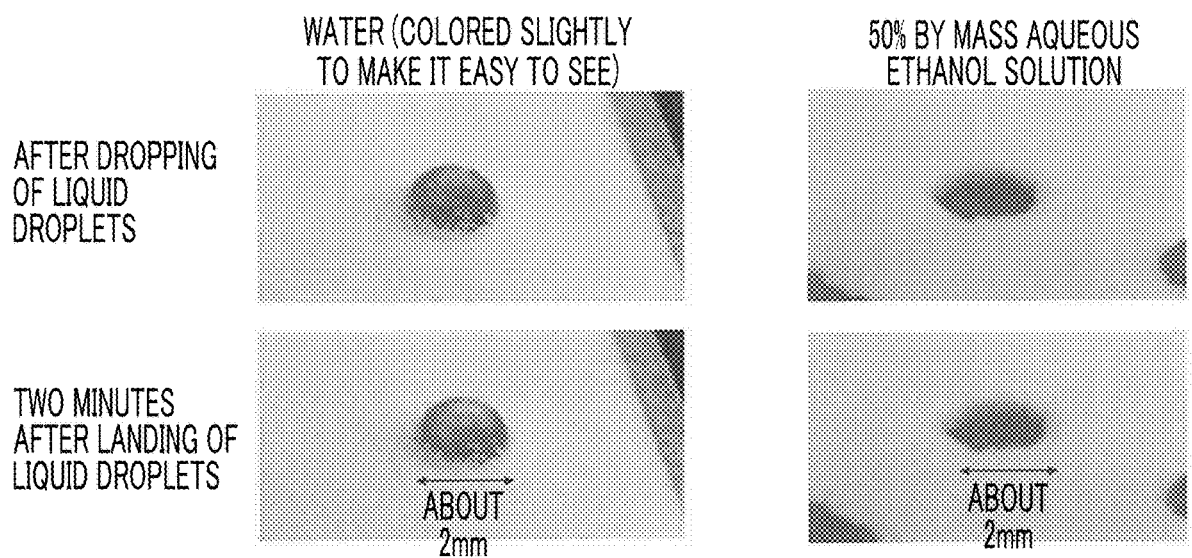
FIG. 20 shows a state after liquid droplets of water or a 50% by mass aqueous ethanol solution are landed on gelatin powders.

FIG. 20 is an observation as to whether or not water and 50% by mass of an aqueous ethanol solution are landed dropwise onto gelatin to permeate therein. In contrast to the liquid droplet of ink jet being 20 μm, FIG. 20 is an experiment on large liquid droplets of about 2 mm. As shown in FIG. 20, since the water does not permeate into the gelatin powder even after 2 minutes and 1 hour from the time immediately after landing, but the aqueous ethanol solution permeates within 1 second after landing, the above contents can be inferred.

Reason 2-2: High speed drawing at a high frequency with a large number of nozzles at a high frequency becomes possible, and therefore the shaping speed increases so that it is easy to produce a high-accuracy formed body.

A typical ink jet head forms a coated surface at high speed with a nozzle array of about 300 dpi to 600 dpi arranged one-dimensionally, and high-speed jetting capacity of about 5 to 20 kHz jetting frequency. In the case of drawing at a high frequency from a large number of nozzles, a large number of liquid droplets are deposited on the gelatin powder in a very short period of time. For example, even in the case where drawing is carried out in a range of 1 cm×1 cm at a relatively low speed of 300 dpi×5 kHz, the drawing is carried out in about 0.02 seconds.

In the case where the drawing is carried out on gelatin powder of about 1 cm×about 1 cm to about 3 cm×about 3 cm using a Z-Printer 310 Plus (300 dpi, assuming that the frequency is 5 kHz or more) and water as the jetting liquid, it is visually observed that liquid droplets of several millimeters in size are formed. Immediately after drawing, since the powder is dry at least at the visual level, so there is no appearance of water permeation, it can be assumed that all the water which is the jetting liquid deposited on the powder coalesces into one large liquid droplet. For this, it can be inferred that, in a system such as gelatin powder in which the outermost surface is hydrophobic rather than hydrophilic, and unevenness corresponding to the particle size are present, the situation called a lotus effect, which causes lotus leaves to repel water droplets against water, occurs so that it becomes a super water repellent state, and water does not easily permeate.

Likewise, drawing about 1 cm×1 cm with water and recoating with a roller to make a 100 μm thickness as one operation (one layer) are repeated about five times (five layers).

Usually, in a 3D printer, it is impossible to obtain a desired formed body for about five layers. As the recoating operation of the roller is repeated about 5 times for 5 layers, water of several millimeters in size on the powder is crushed or pushed into the powder, and therefore the powder starts getting wet. In the case where the powder starts getting wet, the powder laminate starts to be formed starting from the wetted portion, but there are the following two problems, so that it is impossible to produce a high-accuracy formed body.

Reason 2-2-1: In the case of drawing by jetting of the ink from the head, it becomes a formed body in which rod-like bundles of less than 1 mm extending in the scanning direction are gathered, making it impossible to obtain a high-accuracy formed body. This is considered to be landing interference in which the jetted liquid jetted from adjacent nozzles arranged in a line does not permeate into the gelatin powder immediately after landing on the surface of the powder and the jetting liquid of about 10 rows from the nozzle row is gathered on the surface of the powder. In order to prevent landing interference in ordinary ink jet drawing, the surface tension of the jetting liquid is lowered with a surfactant; a dedicated ink jet paper in which fine particles of silica are compounded with a polymer of polyvinyl alcohol is used; or a polyvinyl alcohol polymer is mixed also in powder lamination or the like of gypsum or starch. As in this case, in the case where the permeation into the gelatin powder is slow, it is considered that landing interference occurs extremely and therefore a rod-like bundle is formed. Also, a rod-like bundle will easily peel off in this case of being grabbed by hand. However, the use of an aqueous solution containing alcohols results in rapid permeation into the gelatin powder, so that a rod-like bundle due to landing interference as observed in water is not formed, and a substance close to the desired 3D structure can be formed.

Reason 2-2-2: Extreme lamination shift occurs in water (see FIG. 21), but such lamination shift is greatly alleviated in the case of an aqueous solution mixed with alcohols.

Reason 2-3: Stability of jetted liquid droplet state

In the case where water and ethanol are mixed, the surface tension decreases and the viscosity increases. As a result, it approaches the optimum ink jet jetting conditions, approaches the ideal jetting and flight geometry, and the splitting distance of the leading liquid droplet and the trailing liquid droplet becomes smaller, so that landing of liquid droplets with splitting thereof does not occur in the case of being landed. In addition, since the speed of the trailing liquid droplet is increased, the occurrence frequency of flight bending of the trailing liquid droplet is decreased and therefore the drawing accuracy is improved. In addition, in the case of water, it is possible to jet for the first time with a waveform precisely adjusted with a complicated waveform, but in the case of an aqueous solution mixed with alcohols such as ethanol, it is possible to jet with a simple rectangular wave, and the range of jetting frequency at which jetting is stable can also be expanded. As an example, in the case where 50% by mass of water and 50% by mass of ethanol were mixed, the viscosity increases from 1 cP to 2.8 cP (100 cP=0.1 Pa·s) and the surface tension decreases from 72 mN/m to 28 mN/m as compared with water. Although the optimum viscosity and surface tension vary depending on the ink jet head, the optimum viscosity and surface tension are generally about 3 cP to 12 cP and about 25 to 35 mN/m, respectively, which is close to the proper physical properties. By adding ethanol, it is possible to approximate the optimum physical properties of the jetting liquid without adding a surfactant or a thickener added in a large amount to a general ink jet ink, leading to jetting stabilization. For this reason, the splitting distance of the leading liquid droplet and the trailing liquid droplet becomes smaller, so that landing of liquid droplets with splitting thereof does not occur in the case of liquid droplets being landed. Since the speed of the trailing liquid droplet is increased, the occurrence frequency of flight bending of the trailing liquid droplet is decreased and therefore the drawing accuracy is improved.

Reason 2-4:

It is also assumed that safety is important and nothing other than water is used, but in the case of alcohols having a low boiling point, it is possible to evaporate those alcohols from the powder laminate after shaping, and a structure with high safety can be obtained. Although it varies depending on how to use the gelatin structure for regenerative medical products and the type of gelatin, since the gelatin is often transplanted to the living body after thermal crosslinking at a temperature of about 135° C., alcohols can be removed from the gelatin structures in the case where the boiling point of the alcohols is 120° C. or lower.

(Specific Examples of Alcohols)

Specific examples of alcohols having a boiling point of 120° C. or lower include the following alcohols, but are not particularly limited.

Methanol: boiling point of 65° C.
Ethanol: boiling point of 78° C.
1—Propanol: boiling point of 97° C.
2—Propanol: boiling point of 82° C.
1—Butanol: boiling point of 117° C.
2—Butanol: boiling point of 99° C.
2—Pentanol: boiling point of 119° C.
tert-Butyl alcohol: boiling point of 82° C.

Ethanol is particularly preferred as alcohols having a boiling point of 120° C. or lower.

The mixing ratio of alcohols and water in the aqueous alcohol solution is not particularly limited, but it is generally 10:90 to 90:10, preferably 20:80 to 80:20, more preferably 30:70 to 70:30, and still more preferably 40:60 to 60:40 in terms of mass ratio. For example, the mixing ratio of alcohols and water may be 50:50.

<4> Step b of Producing Gelatin Formed Body including Jetting of Aqueous Alcohol Solution In the present invention, liquid droplets of an aqueous solution containing alcohols having a boiling point of 120° C. or lower are jetted toward the layer formed in the step a from the nozzle and allowed to fly the jetted liquid droplets so that the liquid droplets are landed onto the layer formed in the step a to form a gelatin formed body.

In the present invention, liquid droplets of an aqueous alcohol solution are jetted. The liquid droplets of the aqueous alcohol solution jetted from the nozzle move in the space without contacting either the nozzle or the layer containing a gelatin powder on the substrate.

In the present invention, the temperature in the vicinity of the nozzle in the head is not particularly limited in the case where it is jetted by liquid droplets of an aqueous alcohol solution, but it is preferably 15° C. to 35° C. and more preferably 20° C. to 30° C. In the case where the device is placed at room temperature without environmental and mechanical control, the actuator is driven and the temperature rises, and the temperature in the vicinity of the nozzle in the head is about 28° C. which is slightly higher than the 23° C. environment in the laboratory.

The aqueous alcohol solution can be jetted using an ink jet head having a nozzle. There is known an ink jet recording device that jets ink liquid droplets from a nozzle by an actuator of a piezo element or the like and lands on a medium to form an image on the medium. In the ink jet recording device, it is possible to jet minute ink liquid droplets of several picoliters to 100 picoliters while the density of the arrangement pitch of the nozzles is increased. JP2012-004555A discloses a method and apparatus for producing a functional material by an ink jet method, but the aqueous alcohol solution can be jetted using an ink jet head as described in JP2012-004555A. The disclosure of JP2012-004555A is incorporated herein by reference in its entirety.

The ink jet device can be configured to include a stage on which a substrate is placed and an ink jet head that jets an aqueous alcohol solution toward the substrate.

The stage may be configured to be freely movable in the vertical direction by a moving mechanism, and may further have a moving mechanism in the horizontal direction. As the moving mechanism, for example, a rack and pinion mechanism, a ball screw mechanism, or the like can be used. The stage can be moved to a desired position by controlling the moving mechanism.

The ink jet head jets an aqueous alcohol solution supplied from an ink tank to a desired position of the substrate. A head having a piezo actuator can be used as the ink jet head, but it is not particularly limited.

In the case of powder lamination, movement in the X and Y directions is generally carried out by moving the ink jet head in the X and Y directions while fixing the substrate, but it is sufficient that the ink jet head and the substrate move relative to each other. The ink jet head may be fixed and the substrate may be operated.

The drawing method of the aqueous alcohol solution may be a serial printer method or a line printer method. In order to efficiently draw a large area, a single-pass line printer type apparatus is suitable. In the case of a single pass, the ink can be jetted to the entire surface of each region only by passing through the ink jet head and each region of the substrate onto which ink is deposited once.

As a method of ink jetting, either a continuous type or an on-demand type may be used. In the case of drawing on a large area of several tens of square centimeters or more, an on-demand type with a plurality of nozzles is preferable.

A variety of methods such as a piezo method, a thermal method, a solid method, an electrostatic attraction method, and the like can be used as an actuator that characterizes an on-demand type jetting method. The piezo method can also jet an organic agent-based substance in addition to the water-based substance, and is suitable for jetting an aqueous alcohol solution. In addition, the arrangement of the nozzles may be made in a single row, arranged in a plurality of rows, or arranged in a zigzag lattice pattern.

In the case where a powder flies, a continuous type having a long flight distance of 10 mm or more is suitable. Even in the piezo method in which the flight distance is relatively short, it is also possible to draw with ensuring the flight distance by using an electrostatic field in combination between the head and the substrate.

In the case of controlling and jetting a minute amount of liquid droplets of 1 picoliter or less, it is preferable to use a type that jets the ink from the tip of the needle, which is a type of electrostatic attraction method.

A deaeration module can also be provided between the supply paths from the ink tank to the ink jet head. By using a deaerated aqueous alcohol solution, jetting from the ink jet head can be stabilized. As a deaeration method, a method of passing through a deaeration filter, a method of carrying out an ultrasonic treatment, or the like can be adopted.

The step b of producing a gelatin formed body including jetting of an aqueous alcohol solution can be carried out using, for example, a 3D printer (three-dimensional printer) comprising the ink jet head as described above. Z-Printer 310 Plus (available from 3D Systems Corporation (formerly Z Corporation)) or the like can be used as an example of the 3D printer, which is not particularly limited.

Although the size of the gelatin formed body produced by the method according to the embodiment of the present invention is not particularly limited, in the case where the gelatin formed body is approximated to a rectangular parallelepiped, the length, width, and height of the rectangular parallelepiped are each preferably 0.1 mm to 200 mm and more preferably 1 mm to 100 mm.

<5> Gelatin

The gelatin used in the present invention is preferably a natural gelatin, a recombinant gelatin, or a chemically synthesized gelatin. The natural gelatin refers to a gelatin produced from a naturally occurring collagen. The organism from which the gelatin is derived is not particularly limited. For example, gelatin derived from animals (mammals, fish, and the like) can be used. The gelatin used in the present invention is an animal gelatin or a recombinant gelatin.

The chemically synthesized gelatin refers to an artificially synthesized gelatin. Synthesis of peptides such as gelatin can be either solid phase synthesis or liquid phase synthesis, but it is preferably solid phase synthesis. Solid phase synthesis of peptides is known to those skilled in the art, and examples thereof include Fmoc group synthesis using a fluorenyl-methoxy-carbonyl group (Fmoc group) as protection of an amino group and Boc group synthesis using a tert-butyloxycarbonyl group (Boc group) as protection of an amino group. With regard to the preferred aspect of chemically synthesized gelatin, the contents described in the recombinant gelatin to be described later in the present specification can be applied. The recombinant gelatin will be described later in the present specification.

The hydrophilicity value "1/IOB" value of the gelatin is preferably 0 to 1.0, more preferably 0 to 0.6, and still more preferably 0 to 0.4. IOB is an index for hydrophilicity and hydrophobicity based on the organic conceptual diagram representing the polarity/non-polarity of organic compounds proposed by Atsushi Fujita. The details thereof are described in, for example, "Pharmaceutical Bulletin", vol. 2, 2, pp. 163-173 (1954), "Journal of Japanese Chemistry" vol. 11, 10, pp. 719-725 (1957), and "Fragrance Journal", vol. 50, pp. 79-82 (1981). In short, this process involves assuming that methane ($CH_4$) is the source of all organic compounds and all of the other compounds are methane derivatives, selecting a certain numerical value for each of the number of carbon atoms, substituents, modified moieties, rings and the like thereof, adding the scores to determine an organic value (OV) and an inorganic value (IV), and plotting this value on a diagram with the organic value on the X axis and the inorganic value on the Y axis. IOB on the organic conceptual diagram refers to the ratio of the inorganic value (IV) to the organic value (OV), that is, "inorganic value (IV)/organic value (OV)", on the organic conceptual diagram. For the details of the organic conceptual diagram, refer to "New Edition, The Organic Conceptual Diagram, its Fundamentals and Applications" (Yoshio Koda et al., Sankyo Publishing Co., Ltd., 2008). In the present specification, hydrophilicity and hydrophobicity are indicated by "1/IOB" values, reciprocals of IOB. This notation represents that the smaller the "1/IOB" value becomes (the more the "1/IOB" value approaches 0), the more hydrophilic it is.

In the case of gelatin, its index for hydrophilicity and hydrophobicity indicated by Grand average of hydropathicity (GRAVY) values is preferably −9.0 to 0.3 and more preferably −7.0 to 0.0. The Grand average of hydropathicity (GRAVY) value can be obtained by the methods of "Gasteiger E., Hoogland C., Gattiker A., Duvaud S., Wilkins M. R., Appel R. D., Bairoch A.; Protein Identification and Analysis Tools on the ExPASy Server; (In) John M. Walker (ed): The Proteomics Protocols Handbook, Humana Press (2005). pp. 571-607" and "Gasteiger E., Gattiker A., Hoogland C., Ivanyi I., Appel R. D., Bairoch A.; ExPASy: the proteomics server for in-depth protein knowledge and analysis.; Nucleic Acids Res. 31: 3784-3788 (2003)".

The Gelatin may be crosslinked or non-crosslinked. General known crosslinking methods include thermal crosslinking, crosslinking using aldehydes (for example, formaldehyde and glutaraldehyde), crosslinking using a condensing agent (for example, carbodiimide or cyanamide), enzymatic crosslinking, photocrosslinking, UV crosslinking, hydrophobic interaction, hydrogen bonding, and ionic interaction. In the present invention, the above-mentioned crosslinking method can also be used. The crosslinking method used in the present invention is more preferably thermal crosslinking, UV crosslinking, or enzymatic crosslinking, and is particularly preferably thermal crosslinking.

In the case of carrying out enzymatic crosslinking, the enzyme is not particularly limited as long as it has the effect of crosslinking between polymer materials. The crosslinking can be carried out using preferably transglutaminase and laccase and most preferably transglutaminase. Specific examples of proteins that may be subjected to enzymatic crosslinking with transglutaminase are not particularly limited as long as they are proteins having a lysine residue and a glutamine residue. The transglutaminase may be derived from a mammal or may be derived from a microbe. Specific examples thereof include ACTIVA series manufactured by Ajinomoto Co., Inc., mammal-derived transglutaminase sold as reagents, for example, guinea pig liver-derived transglutaminase, goat-derived transglutaminase, and rabbit-derived transglutaminase manufactured by Oriental Yeast Co., Ltd., Upstate USA Inc., or Biodesign International, Inc., and human-derived blood coagulation factor (Factor XIIIa, manufactured by Haematologic Technologies, Inc.).

The reaction temperature for crosslinking (for example, thermal crosslinking) is not particularly limited as long as crosslinking is possible. The reaction temperature for crosslinking is preferably −100° C. to 500° C., more preferably 0° C. to 300° C., still more preferably 50° C. to 300° C., even more preferably 100° C. to 250° C., and even still preferably 120° C. to 200° C.

The gelatin used in the present invention is particularly preferably a recombinant gelatin.

The recombinant gelatin means a polypeptide or a protein-like substance that is produced by a gene recombination technique and has an amino acid sequence similar to that of gelatin. The recombinant gelatin that can be used in the present invention is preferably one having a repeat of the sequence represented by Gly-X-Y (where X and Y each independently represent any one of amino acids) characteristic of collagen. Here, a plurality of Gly-X-Y sequences may be the same as or different from each other. Preferably, two or more sequences of cell adhesion signals are contained in a molecule. A recombinant gelatin having an amino acid sequence derived from a partial amino acid sequence of collagen can be used as the recombinant gelatin used in the present invention. For example, those described in EP1014176B, U.S. Pat. No. 6,992,172B, WO2004/085473A, and WO2008/103041A can be used, but the recombinant gelatin is not limited thereto. A preferred recombinant gelatin used in the present invention is a recombinant gelatin having the following aspect.

The recombinant gelatin is excellent in biocompatibility based on the inherent performance of natural gelatin, is free from concern for bovine spongiform encephalopathy (BSE) or the like because of being not naturally derived, and is also excellent in non-infectious properties. Moreover, since the recombinant gelatin is homogeneous as compared with natural gelatin and its sequence is determined, it can be designed precisely with little variation in strength or degradability depending on crosslinking or the like.

The molecular weight of the recombinant gelatin is not particularly limited, but it is preferably 2,000 to 100,000 (2 kilodaltons (kDa) to 100 kDa), more preferably 2,500 to 95,000 (2.5 kDa to 95 kDa), still more preferably 5,000 to 90,000 (5 kDa to 90 kDa), and most preferably 10,000 to 90,000 (10 kDa to 90 kDa).

The recombinant gelatin preferably has a repeat of the sequence represented by Gly-X-Y characteristic of collagen. In this context, a plurality of Gly-X-Y sequences may be the same as or different from each other. In Gly-X-Y, Gly represents glycine, and X and Y each represent any amino acid (preferably, any amino acid other than glycine). The Gly-X-Y sequence characteristic of collagen is a very specific partial structure in the amino acid composition and sequence of gelatin and collagen, as compared with other proteins. In this moiety, glycine accounts for approximately 1/3 of the whole composition and appears at a rate of one in every three amino acid residues in the amino acid sequence. Glycine is the simplest amino acid. Its position in the molecular chain is less restricted, and glycine makes a significant contribution to the regeneration of the helix structure in the case of gelation. It is preferred that imino acids (proline or oxyproline) are included in large amounts in the amino acids represented by X and Y and account for 10% to 45% of all the amino acids. Preferably 80% or more, more preferably 95% or more, and most preferably 99% or more of the amino acids in the sequence of the recombinant gelatin are the Gly-X-Y repeat structures.

Commonly available gelatin contains charged polar amino acids and uncharged polar amino acids at a ratio of 1:1. In this context, the polar amino acid specifically refers to cysteine, aspartic acid, glutamic acid, histidine, lysine, asparagine, glutamine, serine, threonine, tyrosine, and arginine. Of them, the polar uncharged amino acid refers to cysteine, asparagine, glutamine, serine, threonine, and tyrosine. The percentage of the polar amino acids is 10% to 40% and preferably 20% to 30% relative to all amino acids constituting the recombinant gelatin used in the present invention. The percentage of uncharged amino acids relative to the polar amino acids is preferably 5% or more and less than 20%, more preferably 5% or more and less than 10%. Further, it is preferred that any one amino acid of serine, threonine, asparagine, tyrosine, or cysteine is not contained in the sequence, and it is more preferred that two or more amino acids of serine, threonine, asparagine, tyrosine, and cysteine are not contained in the sequence.

In general, it is known that a polypeptide contains a minimal amino acid sequence that functions as a cell adhesion signal (for example, "Pathophysiology" Vol. 9, No. 7 (1990), p. 527, Nagai Shoten Co., Ltd.). It is preferable for a single molecule of the recombinant gelatin used in the present invention to have two or more cell adhesion signals. Specifically, amino acids are shown by one-letter notation in a cell adhesion signal. In view of an increase in types of adhering cells, examples of such a sequence are: preferably an RGD sequence, an LDV sequence, an REDV sequence, a YIGSR sequence, a PDSGR sequence, an RYVVLPR sequence, an LGTIPG sequence, an RNIAEIIKDI sequence, an IKVAV sequence, an LRE sequence, a DGEA sequence, and an HAV sequence; more preferably an RGD sequence, a YIGSR sequence, a PDSGR sequence, an LGTIPG sequence, an IKVAV sequence, and an HAV sequence; and particularly preferably an RGD sequence. An ERGD sequence is preferred among the RGD sequence. The amount of the substrate produced by the cell can be improved by using the recombinant gelatin having a cell adhesion signal.

In terms of arrangement of RGD sequences in the recombinant gelatin used in the present invention, it is preferred that the number of amino acids is 0 and 100 and is not uniformly determined between the RGD sequences, and it is more preferred that the number of amino acids is 25 to 60 and is not uniformly determined between the RGD sequences.

From the viewpoint of cell adhesion and growth, the number of such minimal amino acid sequences in a single protein molecule is preferably 3 to 50, more preferably 4 to 30, particularly preferably 5 to 20, and most preferably 12.

In the recombinant gelatin used in the present invention, the percentage of the RGD motifs relative to the total number of the amino acids is preferably at least 0.4%. In the case where the recombinant gelatin contains 350 or more amino acids, it is preferred that each stretch of 350 amino acids contains at least one RGD motif. The percentage of the RGD motifs relative to the total number of the amino acids is more preferably at least 0.6%, still more preferably at least 0.8%, even still more preferably at least 1.0%, particularly preferably at least 1.2%, and most preferably at least 1.5%. The number of RGD motifs in the recombinant peptide is preferably at least 4, more preferably 6, still more preferably 8, and particularly preferably 12 to 16 per 250 amino acids. A percentage of RGD motifs of 0.4% corresponds to at least one RGD sequence per 250 amino acids. The number of RGD motifs is represented by an integer. Therefore, in order to achieve a percentage of RGD motifs of 0.4%, it is necessary for a gelatin consisting of 251 amino acids to contain at least two RGD sequences. The recombinant gelatin of the present invention preferably contains at least 2 RGD sequences per 250 amino acids, more preferably at least 3 RGD sequences per 250 amino acids, and still more preferably at least 4 RGD sequences per 250 amino acids. In a further aspect, the recombinant gelatin of the present invention contains at least 4, preferably 6, more preferably 8, and still more preferably 12 to 16 RGD motifs.

The recombinant gelatin may be partially hydrolyzed.

Preferably, the recombinant gelatin used in the present invention is represented by the formula: A-[(Gly-X-Y)$_n$]$_m$-B. n number of X's each independently represent any one of amino acids, n number of Y's each independently represent any one of amino acids. m represents an integer of preferably 2 to 10 and more preferably 3 to 5. n is an integer of preferably 3 to 100, more preferably 15 to 70, and most preferably 50 to 65. A represents any given amino acid or amino acid sequence, and B represents any given amino acid or amino acid sequence. In addition, n number of Gly-X-Y may be the same as or different from one another.

More preferably, the recombinant gelatin used in the present invention is represented by the formula: Gly-Ala-Pro-[(Gly-X-Y)$_{63}$]$_3$-Gly (in the formula, 63 number of X's each independently represent any one of amino acids, 63 number of Y's each independently represent any one of amino acids. In addition, 63 number of Gly-X-Y may be the same as or different from one another).

It is preferred that a plurality of naturally occurring collagen sequence units are bonded to a repeating unit. The naturally occurring collagen as used herein may refer to any naturally occurring collagen and is preferably type I, type II, type III, type IV, or type V collagen and more preferably type I, type II, or type III collagen. In another embodiment, the origin of the collagen is preferably a human, a cattle, a pig, a mouse, or a rat and more preferably a human.

The isoelectric point of the recombinant gelatin used in the present invention is preferably 5 to 10, more preferably 6 to 10, and still more preferably 7 to 9.5. The measurement of the isoelectric point of the recombinant gelatin can be carried out by measuring the pH after passing a 1% by mass of gelatin solution through a mixed bed column of a cation-anion exchange resin as described in the isoelectric focusing method (refer to Maxey, C. R. (1976); Phitogr. Gelatin 2, Editor Cox, P. J. Academic, London, Engl.).

Preferably, the recombinant gelatin is not deaminated.

Preferably, the recombinant gelatin does not have a telopeptide.

Preferably, the recombinant gelatin is a substantially pure polypeptide prepared by a nucleic acid encoding an amino acid sequence.

The recombinant gelatin used in the present invention is particularly preferably any one of:

(1) a peptide consisting of an amino acid sequence as set forth in SEQ ID NO: 1;

(2) a peptide consisting of an amino acid sequence in which one or several amino acids are deleted, substituted, or added in the amino acid sequence as set forth in SEQ ID NO: 1, and having biocompatibility; or (3) a peptide consisting of an amino acid sequence having 80% or more (more preferably 90% or more, particularly preferably 95% or more, and most preferably 98% or more) sequence identity to the amino acid sequence as set forth in SEQ ID NO: 1, and having biocompatibility.

The sequence identity in the present invention refers to the value calculated by the following equation.

$$\% \text{ sequence identity} = [(\text{number of identical residues})/(\text{alignment length})] \times 100$$

The sequence identity in the two amino acid sequences can be determined by any method known to those skilled in the art, for which a basic local alignment search tool (BLAST) program (J. Mol. Biol. 215: 403-410, 1990) or the like can be used.

"One or several" in the "amino acid sequence in which one or several amino acids are deleted, substituted, or added" preferably means 1 to 20 amino acids, more preferably 1 to 10 amino acids, still more preferably 1 to 5 amino acids, and particularly preferably 1 to 3 amino acids.

The recombinant gelatin used in the present invention can be produced by a gene recombination technique known to those skilled in the art and can be produced according to a method described in, for example, EP1014176A2, U.S. Pat.

No. 6,992,172B, WO2004-085473A, or WO2008/103041A. Specifically, a gene encoding an amino acid sequence of predetermined recombinant gelatin is acquired, the acquired gene is incorporated into an expression vector to construct a recombinant expression vector, which is then introduced into a suitable host to construct a transformant. The resulting transformant is cultured in a suitable medium, whereby the recombinant gelatin is produced. Thus, the produced recombinant gelatin can be recovered from the culture to prepare the recombinant gelatin used in the present invention.

<6> Lamination

The method for producing a gelatin formed body according to the embodiment of the present invention may further include, after the step b, a step c of forming a layer containing a powder which is obtained by air-drying an aqueous gelatin solution and has an average particle diameter of 25 to 200 μm on the layer formed in the step a and the gelatin formed body formed in the step b; and a step d of jetting liquid droplets of an aqueous solution containing alcohols having a boiling point of 120° C. or lower from a nozzle and flying the jetted liquid droplets so that the liquid droplets are landed on the layer formed in the step c, thereby producing a gelatin formed body.

In the case of laminating as described in the step c and step d, there are cases where displacement of layers, adhesion of layers to the roller surface, and the like may occur, but in the present invention, the above problems can be solved and excellent recoatability can be achieved.

The step c can be carried out in the same way as in the step a. The types of materials used in the step c may be the same as or different from those in the step a, but are preferably the same as those in the step a. The gelatin in the step c is preferably an animal gelatin or a recombinant gelatin.

The step d can be carried out in the same way as in the step b. The types of materials used in the step d may be the same as or different from those in the step b, but are preferably the same as those in the step b.

As in the case of the step b, the alcohol to be used in the step d is particularly preferably ethanol.

In the case of carrying out the step c and the step d, the number of times is not particularly limited, and the steps can be carried out at any number of times of one or more times, for example, 1 to 3,000 times.

<7> Method of Forming by Lamination (7-1) First Lamination Method of Present Invention According to a preferred aspect of the present invention, a gelatin formed body can be produced in such a way that the gelatin formed body produced in the step b is in contact with the substrate.

Figure 17A:
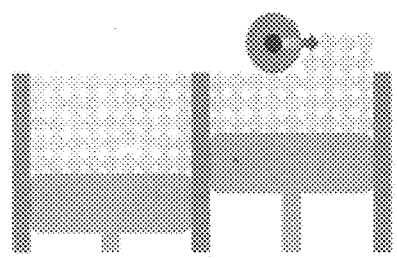
FIGS. 17A to 17E show a method for producing a formed body by a conventional method.
Figure 17B:
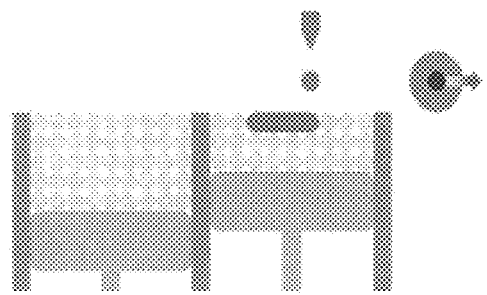
Figure 17C:
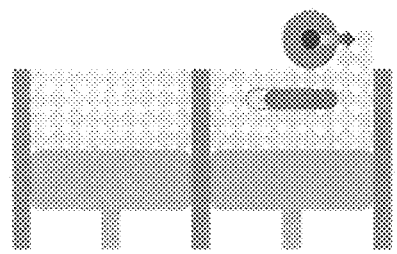
Figure 17D:
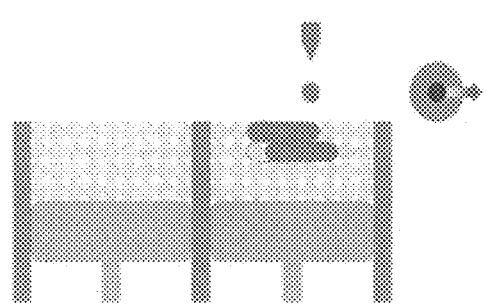
Figure 17E:
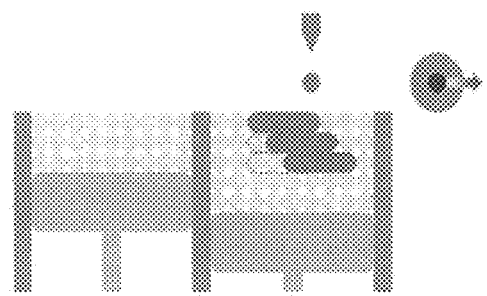

A method for producing a formed body by a conventional method is shown in FIGS. 17A to 17E. FIG. 17A is a step a of forming a layer containing a powder on a substrate. FIG. 17B is a step of jetting liquid droplets of the aqueous alcohol solution toward the layer formed in the step a from a nozzle and flying the jetted liquid droplets so that the liquid droplets are landed on the layer formed in the step a, thereby forming a gelatin formed body. In FIG. 17B, the formed body of the first layer is formed. In the method shown in FIGS. 17A to 17E, the formed body of the first layer is not in contact with the substrate, and the powder is present under the formed body of the first layer (formed body including the layer first formed). In this state, as shown in FIG. 17C, in the case where a layer containing the powder of the second layer is formed as step c, the position of the formed body of the first layer is shifted. After that, as shown in FIG. 17D, in the case where the step d is carried out, the second layer formed body is formed at a position deviated from the first layer formed body. In the same manner as described above, as shown in FIG. 17E, the positions of formed bodies of the third and subsequent layers are also deviated from the positions of the formed body of the first layer and the formed body of the second layer. Such a phenomenon that the position of the formed body is shifted as described above occurs conspicuously in the case where a gelatin powder having a light mass is used.

Figure 18A:
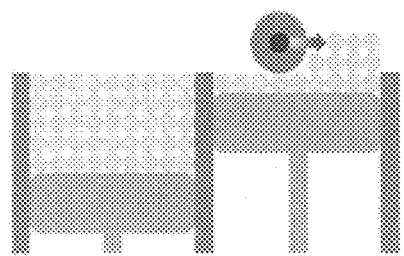
FIGS. 18A to 18E show a method for producing a formed body by a first lamination method of the present invention.
Figure 18B:
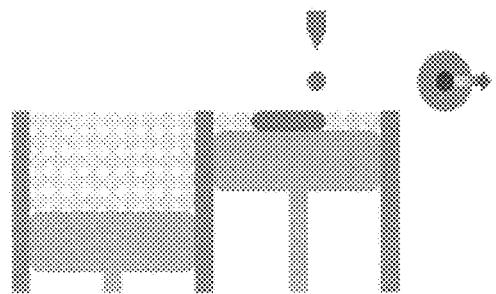
Figure 18C:
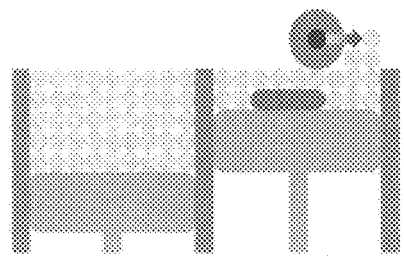
Figure 18D:
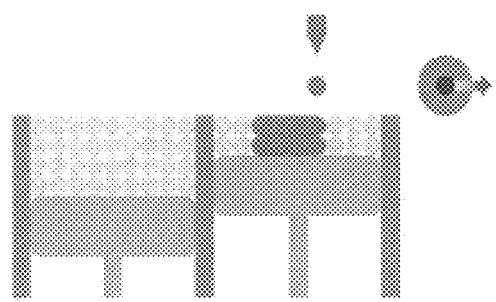
Figure 18E:
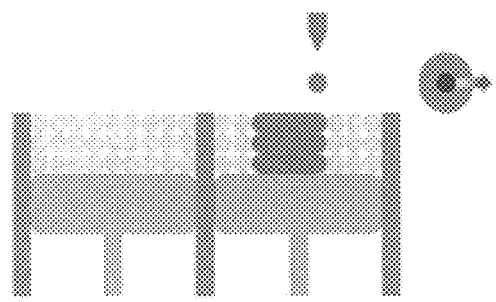

On the other hand, a method for producing a formed body by the first lamination method of the present invention is shown in FIGS. 18A to 18E. FIG. 18A is a step a of forming a layer containing a powder on a substrate, but the thickness of the layer containing a powder is made substantially the same as the thickness of the formed body of the first layer. By forming the powder-containing layer in this manner, as shown in FIG. 18B, in the case where the formed body of the first layer (formed body including the layer first formed) is formed (step b), the formed body of the first layer is brought into contact with the substrate and the powder is not present under the formed body of the first layer. By adopting the above state, as shown in FIG. 18C, even in the case where a powder-containing layer of the second layer is formed as step c, it is possible to prevent the position of the first-layer formed body from being displaced. As a result, as shown in FIGS. 18D and 18E, the formed bodies of the second and subsequent layers can be formed at the same position as that of the formed body of the first layer without being displaced.

According to the present invention, there is provided a method for producing a formed body, including:

a step a of forming a layer containing a powder on a substrate; and a step b of jetting liquid droplets toward the layer formed in the step a from a nozzle and flying the jetted liquid droplets so that the liquid droplets are landed on the layer fanned in the step a, thereby forming a formed body (here, the formed body formed is in contact with the substrate).

Further, according to the present invention, there is provided a method for producing a formed body, including:

a step a of forming a layer containing a powder on a substrate;

a step b of jetting liquid droplets toward the layer formed in the step a from, a nozzle and flying the jetted liquid droplets so that the liquid droplets are landed on the layer formed in the step a, thereby forming a formed body (here, the formed body formed is in contact with the substrate);

a step c of forming a layer containing a powder on the layer formed in the step a and the formed body formed in the step b, after the step b; and a step d of jetting liquid droplets from a nozzle and flying the jetted liquid droplets so that the liquid droplets are landed on the layer formed in the step c, thereby producing a formed body.

(7-2) Second Lamination Method of Present Invention

In a further preferred aspect, the method for producing a gelatin formed body according to the embodiment of the present invention is such that the method further includes, after the step b, a step c1 of forming a layer containing a powder which is obtained by air-drying an aqueous gelatin solution and has an average particle diameter of 25 to 200 μm on the layer formed in the step a and the gelatin formed body formed in the step b; and a step d1 of jetting liquid droplets of an aqueous solution containing alcohols having a boiling point of 120° C. or lower from a nozzle and flying the jetted liquid droplets so that the liquid droplets are landed on the layer formed in the step c1, thereby producing a gelatin formed body, and the method further includes, after the step d1, a step e of forming a layer containing a powder which is obtained by air-drying an aqueous gelatin solution and has an average particle diameter of 25 to 200 µm on the layer formed in the step c1 and the gelatin formed body formed in the step d1; and a step f of jetting liquid droplets of an aqueous solution containing alcohols having a boiling point of 120° C. or lower from a nozzle and flying the jetted liquid droplets so that the liquid droplets are landed on the layer formed in the step e, thereby producing a gelatin formed body, in which, in the step b, the produced gelatin formed body is in contact with the substrate, in the step d1, the liquid droplets are landed on a region corresponding to the outer peripheral region of the upper surface of the gelatin formed body formed in the step b, and in the step f, the liquid droplets are landed in a region corresponding to the outer peripheral region of the upper surface of the gelatin formed body formed in the step d1 and in a region inside the region surrounded by the gelatin formed body farmed in the step d1.

In the method of the above aspect, by forming a formed body in the shape of a box and a Banned body (desired formed body) inside the box, it is possible for the formed body in the shape of a box from to prevent the formed body inside from being displaced. The formed body in the shape of a box is formed so as not to deviate from the position of the formed body of the first layer by using the method described in the first lamination method of the present invention. In addition, the internal formed body is not connected to the formed body in the shape of a box (that is, the bottom surface and the side surface of the internal formed body are not in contact with the formed body in the shape of a box). In the method described in the first lamination method of the present invention, there is a concern that the shape of the formed body may collapse depending on the operation in the case where the desired formed body is formed and then peeled off from the substrate, and therefore careful operation is required. However, according to the second lamination method of the present invention, the desired formed body (internal formed body) can be easily obtained without collapsing the shape thereof. That is, since no force is applied in the case of separating the internal formed body from the powder-containing layer, it is possible to produce a minute formed body having a total length of several millimeters, a formed body having a large number of pores, or a thin formed body having a thickness of several hundreds of micrometers. Further, according to the second lamination method of the present invention, a spherical formed body having a curved surface can be produced as the structure of the underlayer (first layer).

Figure 19A:
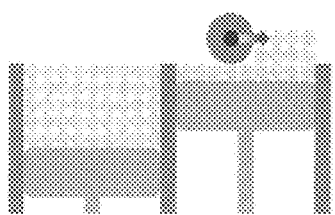
FIGS. 19A to 19F show a method for producing a formed body by a second lamination method of the present invention.
Figure 19B:
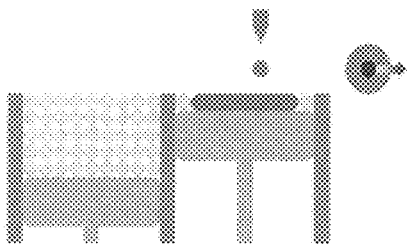
Figure 19C:
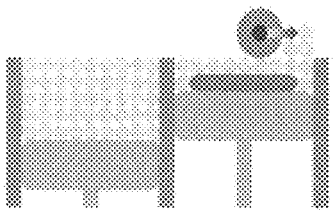
Figure 19D:
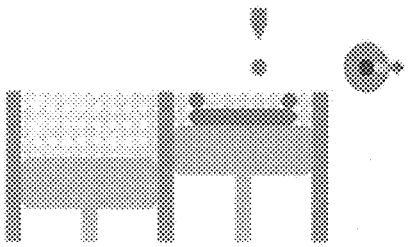

A method for producing a formed body by the second lamination method of the present invention is shown in FIGS. 19A to 19F. FIG. 19A is a step a of forming a layer containing a powder on a substrate, but the thickness of the layer containing a powder is made substantially the same as the thickness of the formed body of the first layer of the box-shaped formed body. By forming the powder-containing layer in this manner, as shown in FIG. 19B, in the case where the formed body of the first layer of the box-shaped formed body (formed body including the layer first formed) is formed (step b), the first-layer formed body is brought into contact with the substrate and the powder is not present under the formed body of the first layer. By adopting the above state, as shown in FIG. 19C, even in the case where a powder-containing layer of the second layer of the box-shaped formed body is formed as step c1, it is possible to prevent the position of the first-layer fanned body of the box-shaped formed body from being displaced. FIG. 19D shows a step d1 of producing a gelatin formed body by jetting liquid droplets from a nozzle and causing the liquid droplets to fly and land on the layer formed in the step c1. In FIG. 19D, the liquid is landed in a region corresponding to the outer peripheral region of the upper surface of the formed body.

Figure 19E:
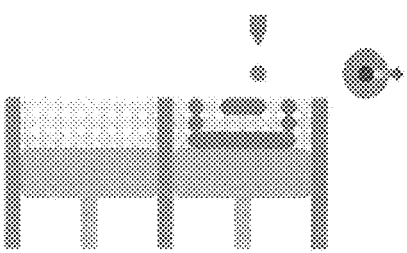
Figure 19F:
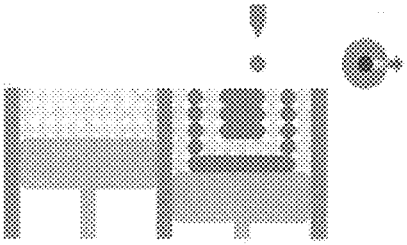

FIG. 19E shows, after carrying out a step e of forming a layer containing a powder on the layer formed in the step c1 and the gelatin formed body formed in the step d1, a step f of jetting liquid droplets from a nozzle and flying the jetted liquid droplets so that the liquid droplets are landed on the layer formed in the step e, thereby producing a gelatin formed body. In the step f, the liquid is landed on a region inside the region surrounded by the gelatin formed body formed in the step d1, whereby an internal formed body can be formed. FIG. 19F shows that, by repeating the steps e and f, an (internal) formed body having a desired shape is formed inside the Rolled body in the shape of a box.

According to the present invention, there is provided a method for producing a formed body, including:

a step a of forming a layer containing a powder on a substrate; a step b of jetting liquid droplets toward the layer formed in the step a from a nozzle and flying the jetted liquid droplets so that the liquid droplets are landed on the layer fanned in the step a, thereby forming a formed body (the formed body produced in step b is in contact with the substrate); a step c1 of forming a layer containing a powder on the layer formed in the step a and the formed body formed in the step b, after the step b;

a step d1 of jetting liquid droplets from a nozzle and flying the jetted liquid droplets so that the liquid droplets are landed on the layer formed in the step c1, thereby producing a fanned body (in the step d1, the liquid droplets are landed in a region corresponding to the outer peripheral region of the upper surface of the formed body formed in the step b); and after the step d1, a step e of forming a layer containing a powder on the layer formed in the step e1 and the formed body formed in the step d1; and a step f of jetting liquid droplets from a nozzle and flying the jetted liquid droplets so that the liquid droplets are landed on the layer formed in the step e, thereby producing a formed body (in the step f, the liquid droplets are landed in a region corresponding to the outer peripheral region of the upper surface of the gelatin formed body formed in the step d1 and a region inside the region surrounded by the formed body formed in the step d1).

<8> Step of Removing Powder

In the present invention, a step g of removing the powder not used for forming a gelatin formed body can be further included. Removing the powder is to remove the powder from the surface of the formed body.

By removing the gelatin powder which is not used for the formation of a formed body, it is possible to recover the formed body formed into a desired shape.

The method of removing the gelatin powder which is not used for the formation of a formed body is not particularly limited, and it may be carried out using compressed air, for example.

<9> Step of Curing Formed Body

In the present invention, a step h of heating the formed body to cure the formed body can be further included after the step g of removing the gelatin powder which is not used for the formation of a formed body.

By carrying out the step h, the strength of the formed body can be increased.

The step h of heating the formed body to cure the formed body can be carried out by heating the formed body at a temperature of generally 50° C. to 300° C., preferably 100° C. to 250° C., and more preferably 120° C. to 200° C. In this regard, T [Kelvin: K]=t [Celsius degree: ° C.] +273.15. The heating of the formed body can be carried out in an environment such as air, inert gas, or vacuum, but it is preferable to carry out in a low oxygen environment. Among them, heating is preferably carried out in an inert gas such as nitrogen from the viewpoint of heating uniformity.

The heating time is not particularly limited, but it is generally 1 hour to 72 hours, preferably 2 hours to 48 hours, and more preferably 4 hours to 28 hours.

In the present invention, a step i of encapsulating the formed body by means of a support such as a mesh can be further included after the step h of curing the formed body by heating. The step i facilitates maintaining the shape of the formed body in a wet environment.

The material for the support such as a mesh is not particularly limited, but in the case of being applied to a living body, it is preferable to use a biocompatible material. For example, a polymer may be used.

In this formed body, even in the case where the formed body cannot maintain its shape due to a wet environment or the like, the shape can be maintained as long as a support such as a mesh surrounds the formed body. In addition, a support such as a mesh supports the formed body in a state of communicating with the outside, and in the case where the formed body encapsulated by the support such as a mesh is transplanted into a living body, the surrounding living tissue can access the formed body through the support.

<10> Step of Seeding Cells into Formed Body

In the present invention, a step j of seeding cells into a formed body can be further included.

The application of the formed body in the present invention is intended for use as a scaffold for regenerative medicine or a tissue repair material as described later, but it is assumed for a case in which the formed body is used with seeding of cells and a case where the formed body is used without seeding of cells.

The type of cell to be seeded is not particularly limited, and can be selected as appropriate depending on the purpose of use.

The cell used is preferably an animal cell, more preferably a vertebrate-derived cell, and particularly preferably a human-derived cell. The type of the vertebrate-derived cell (particularly, a human-derived cell) may be any of a pluripotent cell, a somatic stem cell, a precursor cell, and a mature cell. For example, an embryonic stem (ES) cell, a germline stem (GS) cell, or an induced pluripotent stem (iPS) cell can be used as the pluripotent cell. For example, a mesenchymal stem cell (MSC), a hematopoietic stem cell, an amniotic cell, an umbilical cord blood cell, a bone marrow-derived cell, a cardiac muscle stem cell, an adipose-derived stem cell, or a neural stem cell can be used as the somatic stem cell. For example, cells derived from the skin, dermis, epidermis, muscle, cardiac muscle, nerve, bone, cartilage, endothelium, brain, epithelium, heart, kidney, liver, pancreas, spleen, oral cavity, cornea, bone marrow, umbilical cord blood, amnion, or hair can be used as the precursor cell and the mature cell. For example, an ES cell, an iPS cell, MSC, a cartilage cell, an osteoblast, an osteoprogenitor cell, a mesenchyme cell, a myoblast, a cardiac muscle cell, a cardiac myoblast, a nerve cell, a hepatic cell, a beta cell, a fibroblast, a corneal endothelial cell, a vascular endothelial cell, a corneal epithelial cell, an amniotic cell, an umbilical cord blood cell, a bone marrow-derived cell, or a hematopoietic stem cell can be used as the human-derived cell. In addition, the origin of the cells may be either an autologous cell or a heterologous cell.

<11> Application of Gelatin Formed Body Produced by Method of Present Invention

The application of the gelatin formed body produced by the method for producing a gelatin formed body according to the embodiment of the present invention is not particularly limited, but it is preferably a scaffold for regenerative medicine or a tissue repair material. The application of the gelatin formed body will be described later in the present specification.

[2] Gelatin Formed Body

The present invention further provides a gelatin formed body produced by the method for producing a gelatin formed body according to the embodiment of the present invention described in the foregoing section [1].

The gelatin formed body according to the embodiment of the present invention can be produced with high shaping accuracy.

The application of the gelatin formed body according to the embodiment of the present invention is not particularly limited. For example, the gelatin formed body of the present invention can be used as a scaffold for regenerative medicine, a regenerative medicine product (ex vivo tissue culture), or a tissue repair material, preferably as a scaffold for regenerative medicine or a tissue repair material, and particularly preferably as a tissue repair material for bone regeneration.

The tissue repair material in the present invention refers to a material that contributes to the formation of tissues at the site of implantation by being implanted in a living body and may or may not contain cells. Further, the tissue repair material may or may not contain a component that promotes the reaction of a living body such as a growth factor or a drug. Further, the gelatin formed body according to the embodiment of the present invention may be used in admixture with an inorganic material such as hydroxyapatite, or may be used as a composite with such an inorganic material.

The tissue repair material in the present invention includes materials that promote the formation of abnormal tissues including scar tissue and the like as well as those that contribute to the formation of normal tissues normally present at the site of implantation.

Specific examples of the tissue repair material include, but are not particularly limited to, cartilage, meniscus, skin, or bone repair materials. That is, the gelatin formed body according to the embodiment of the present invention can be used as a therapeutic agent for regenerating cartilage, meniscus, skin, or bone. As long as the above-mentioned regeneration is necessary, the disease is not limited, but as one example, diseases accompanying cartilage defect include arthrosis deformans, osteochondral defect, osteochondritis dissecans, traumatic cartilage damage, osteoarthritis, recurrent polychondritis, chondrodystrophia foetalis, intervertebral disc damage, and intervertebral disc hernia.

The gelatin formed body according to the embodiment of the present invention can be used as a therapeutic agent for bone regeneration in combination with a transplantation cell or an osteoinductive agent. Examples of the osteoinductive agent include, but are not particularly limited to, a bone morphogenetic protein (BMP) and basic fibroblast growth factor (bFGF).

Since the gelatin formed body according to the embodiment of the present invention can be used as a tissue repair material, a method of repairing a tissue and a method of treating a disease accompanied by tissue damage are also encompassed by the present invention. The tissue repair method in the present invention includes applying a tissue repair material which is a gelatin formed body to a site where the target tissue is missing or damaged, and may include another step as necessary. Another step may be, for example, applying a transplantation cell and/or an osteoinductive agent to the site to which a tissue repair material is applied, before or after application of the tissue repair material or simultaneously with application of the tissue repair material.

Incision, injection, arthroscopy, endoscopy, or the like can be used as a method of applying a gelatin formed body to the site where the target tissue is missing or damaged.

The void volume of the gelatin formed body according to the embodiment of the present invention is not particularly limited and is generally 10% to 90%, preferably 10% to 70%, more preferably 20% to 40%, and still more preferably 25% to 35%. The void volume can be obtained by carrying out microfocus CT analysis of the gelatin formed body to measure a filling rate at the upper, middle, and lower positions in the thickness direction 2 points each position, 6 points in total, followed by calculation from the measured filling rate by the following equation.

Void volume=100%−filling rate

It is preferred that the gelatin formed body according to the embodiment of the present invention has pores communicating with the external space. In the case where the gelatin formed body having pores is transplanted into the living body, the cells are likely to enter the inside of the gelatin formed body. It is more preferred that the pore communicating with the external space passes through the inside of the formed body and is in communication with the external space at both ends of the pore.

The representative diameter of the pore communicating with the external space is not particularly limited, but it is preferably 300 µm to 2000 µm. The definition and measurement method of the representative diameter are as follows.

A vertical cross section is taken with respect to a pore extending from the outer edge portion of the formed body to the inner portion, and in the case where the shape can be approximated by a circle, the diameter thereof is taken as the representative diameter and in the case where it is appropriate for the shape to be approximated by an ellipse, the short side thereof is taken as the representative diameter. Also in the case of a quadrangular shape, the representative diameter shall be the length of one side of the shorter side. The actual pore fluctuates in the depth direction of the pore, but in the case where the fluctuation is relatively small, the representative diameter is represented by the size of the pore seen at the outer edge portion of the formed body. In the case where the pore diameter is changed by design, the diameter at the place where it is the smallest is taken as the representative diameter. In the case where the pore is at a dead end, measurement is not carried out until 100 m from the dead end.

In the case where there is a large fluctuation in the depth direction, measure the diameter at the constricted part and use it as the representative diameter.

In the case of measuring the outer edge portion of the formed body, the outer edge portion is measured with a measurable microscope. In the case of measuring the inside of the formed body, the section is cut off with a microtome or the like so as not to distort the formed body, and the pore size is measured with a microscope. The representative diameter may be measured from cross-sectional data of microfocus CT. In that case, since the absolute accuracy of the length of the cross-sectional data of the microfocus CT is low, the pore size is obtained by measuring the length of the whole length of the formed body and the vicinity of the mark with a microscope and referring to data and the like.

The pore communicating with the external space indicates that the pore is formed in the space inside the formed body from one surface of the formed body. That is, the space inside the pore communicates with the external space.

The expression "the pore communicating with the external space passes through the inside of the formed body and is in communication with the external space at both ends of the pore" indicates that the pore is formed in the space inside the formed body from the surface of a certain portion of the formed body and further communicates with the external space through the surface of another portion of the formed body.

The present invention will be described in more detail with reference to the following Examples, but the present invention is not limited by the Examples.

EXAMPLES

[Recombinant Gelatin]
CBE3 (described in WO2008/103041A) given below was prepared as a recombinant gelatin.
CBE3
Molecular weight: 51.6 kD
Structure: GAP[(GXY)$_{63}$]$_3$G
Number of amino acids: 571
Number of RGD sequences: 12
Imino acid content: 33%

Almost 100% of amino acids are GXY repeating structures. The amino acid sequence of CBE3 does not contain any of serine, threonine, asparagine, tyrosine, and cysteine. CBE3 has an ERGD sequence.
Isoelectric point: 9.34
GRAVY value: −0.682
1/IOB value: 0.323

Amino acid sequence (SEQ ID NO: 1 in the Sequence Listing) (This amino acid sequence corresponds to the amino acid sequence shown in SEQ ID NO: 3 in WO2008/103041A. Note that "X" at the end was modified to "P")

GAP (GAPGLQGAPGLQGMPGERGAAGLPGPKGERGDAGPKGADGA

PGAPGLQGMPGERGAAGLPGPKGERGDAGPKGADGAPGKDGVRGLAGPIG

PPGERGAAGLPGPKGERGDAGPKGADGAPGKDGVRGLAGPIGPPGPAGAP

GAPGLQGMPGERGAAGLPGPKGERGDAGPKGADGAPGKDGVRGLAGPP)$_3$

G

[Method of Measuring Average Particle Diameter in Examples]

The particle size distribution of the gelatin powder was measured using a laser diffraction/light scattering type particle size distribution analyzer LA920 (available from Horiba Corporation). Specific procedure was as follows: a sample container was filled with anhydrous special grade ethanol (available from Wako Pure Chemical Industries, Ltd.) as a dispersion solvent, a gelatin powder to be measured was gradually added and dispersed therein while ultrasonic waves are applied, and then the measurement was started in the case where the light transmittance reached a predetermined range. From the obtained particle size distribution data, the median diameter was read and this value was taken as the average particle diameter.

(1) Production of Gelatin Powder

Air-Dried Gelatin Powder

The above recombinant gelatin was dissolved in water for injection at 50° C. to obtain a 20% by mass of aqueous solution. After defoaming the solution under reduced pressure, 14 mL each was dispensed into a 12.5×8.5 cm tray made of polypropylene, followed by drying at room temperature for 72 hours. The obtained dried film was cut into about 2 cm square. Next, the above-obtained gelatin air-dried solid was pulverized to 1 mm or less using a QUADRO COMIL U5 (available from Powrex Corporation) which is a type of a high-speed rotary type mill as a first stage pulverizing, and then was pulverized so as to have a desired average particle diameter of a level of several tens of micrometers using a Dry Burst Mini (available from Sugino Machine Limited) which is a high-speed rotary type impeller mill.

Freeze-Dried Gelatin Powder

The above recombinant gelatin was dissolved in water for injection at 50° C. to obtain a 4% by mass of aqueous solution. After defoaming the solution under reduced pressure, 8 mL each was dispensed into a tray made of poly(tetrafluoroethylene) having an inner diameter of 4.5 cm, uniformly frozen, and then freeze-dried at -20° C. for 72 hours. The resulting dried body was cut into about 1 cm square. Next, the above-obtained gelatin air-dried solid was pulverized to 1 mm or less using a QUADRO COMIL U5 (available from Powrex Corporation) which is a type of a high-speed rotary type mill as a first stage pulverizing, and then was pulverized so as to have a desired average particle diameter of a level of several tens of micrometers using a Dry Burst Mini (available from Sugino Machine Limited) which is a high-speed rotary type impeller mill.

(2) Jetting Liquid (Ink)

As the jetted liquid, water or an aqueous ethanol solution (50% by mass of water and 50% by mass of ethanol) was used.

(3) Production of Formed Body (Comparison between Air-Dried Powder and Freeze-Dried Powder)

The gelatin powder produced in the section (1) was introduced into a FujiFilm Dimatix Materials Printer (DMP-2831), in which the liquid droplet jetting amount was about 10 pL, the number of nozzles was 5, and the jetting frequency was set to 4 kHz. A 4 mm formed body was produced in the head main scanning direction. The direction in which the scanning movement is carried out while jetting the head is defined as the head main scanning direction, and the direction perpendicular to the main scanning direction of the head and moving and scanning without jetting is defined as the head sub-scanning direction. The lamination pitch of the gelatin powder was set to 10 μm. *The X direction in the figure and the head main scanning direction are the same.

In the above-mentioned construction of the formed body, a formed body having a predetermined size is produced by repeating a step of forming a layer containing a gelatin powder on a substrate, and a step of jetting the jetting liquid from the nozzle in a liquid droplet state to land on the layer containing a gelatin powder, thereby producing the gelatin formed body.

Figure 2:
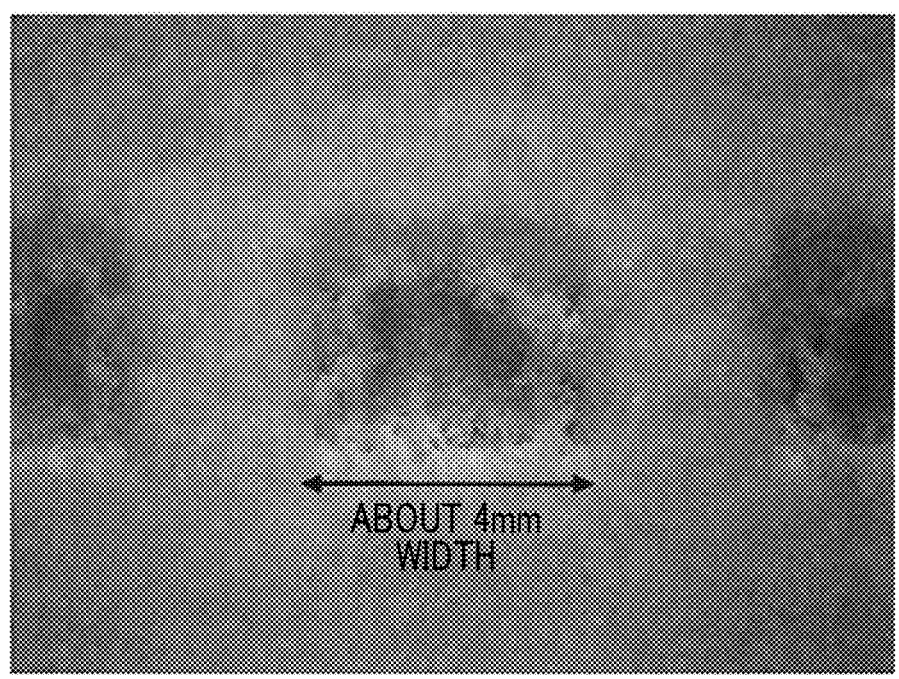
FIG. 2 shows a formed body produced using a freeze-dried gelatin powder.

FIG. 1 shows a formed body produced by using an air-dried gelatin powder, and FIG. 2 shows a formed body produced by using a freeze-dried gelatin powder. In the formed body shown in FIG. 1, the film is not substantially lower than the surface of the powder in the vertical direction (Z direction). Also, the film is reduced by about 20% in one direction (X direction) of the plane. In the formed body shown in FIG. 2, the entire film is lower by about 500 μm than the surface of the powder so that the bottom of the container can be seen. Also, the film is reduced by half (about 50%) in one direction (X direction) of the plane.

(4) Evaluation of Relationship between Average Particle Diameter of Powder and Composition of Aqueous Solution and Film Thickness and Shrinkage Ratio As gelatin particles, fish gelatin particles (gelatin made from fish is used to prepare particles in the same manner as CBE3) (recombinant gelatin simulated particles) were used. Using fish gelatin having an average particle diameter of 21 μm, 54 μm or 68 μm and water or an aqueous ethanol solution (50% by mass of water and 50% by mass of ethanol) as a jetting liquid, and using a FujiFilm Dimatix Materials Printer (DMP-2831), in which the liquid droplet jetting amount was about 10 pL, the number of nozzles was 5, and the jetting frequency was set to 4 kHz, formed bodies having various film thicknesses shown in FIG. 3 were constructed in the head main scanning direction and the shrinkage ratio was measured.

The film thickness of the formed body was measured by taking an average of 5 or more points in the cross-sectional direction of the film by a microscope.

The shrinkage ratio was measured with a microscope immediately after film formation, by measuring the distance from the edge to the edge in the X direction of the film and the distance from the edge to the edge where the trace of landing remained.

The relationship between film thickness and shrinkage ratio is shown in FIG. 3. In FIG. 3, A to E show the following.

A: Fish gelatin particles having an average particle diameter of 68 μm; and jetting liquid: aqueous ethanol solution (50% by mass of water and 50% by mass of ethanol)

B: Fish gelatin particles having an average particle diameter of 68 μm; and jetting liquid: water C: Fish gelatin particles having an average particle diameter of 54 μm; and jetting liquid: water D: Fish gelatin particles having an average particle diameter of 21 μm; and jetting liquid: water E: Commercially available starch (ZP12e, manufactured by Z Corporation); and jetting liquid: water It can be seen that the shrinkage ratio deteriorates (increases) in the case where particles having an average particle diameter of 21 μm are used. In addition, even in the case where particles having an average particle diameter of 54 μm or 68 μm are used, it can be seen that in the case where water is used as the jetting liquid, the shrinkage ratio deteriorates as the film thickness increases. On the other hand, in the case where particles having an average particle diameter of 54 μm or 68 μm are combined with an aqueous ethanol solution, an increase in shrinkage ratio is suppressed even in the case where the film thickness increases, whereby good results are obtained.

(5) Evaluation of Recoatability

The recoatability was evaluated using recombinant gelatin simulated particles having an average particle diameter of 21 μm, 54 μm, or 68 μm. Specifically, the case where a fluidity index (v1/σc), which is determined by the ratio between the consolidation stress (σ1) and the non-pressure yield stress (σc) using a powder fluidity tester (powder flow tester, manufactured by Brookfield Engineering Laboratories, Inc.), is 4 or more was evaluated as good in recoatability.

The results of the evaluation of the recoatability are shown in Table 1 below.

TABLE 1

| Average particle diameter of powder | Recoatability | Details of recoatability |
|---|---|---|
| 68 μm | Good | Powder surface is approximately flat |
| 54 μm | Good | Powder surface is approximately flat |
| 21 μm | Poor | Occurrence of unevenness on powder surface by adhesion of powder to roller |

(6) Evaluation of Deviation During Lamination by Jetting Liquid

A gelatin formed body was produced using CBE3 particles having an average particle diameter of 48 μm, water or an aqueous ethanol solution as a jetting liquid, and a Z-Printer 310 Plus (available from 3D Systems Corporation (formerly Z Corporation)). The produced gelatin formed body is shown in FIG. 4.

In the case where water is used as the jetting liquid, layer misalignment occurs at the time of lamination, but in the case where aqueous ethanol solution is used as the jetting liquid, no layer misalignment has occurred.

(7) Production of Formed Body Having Voids

A formed body having voids was produced using CBE3 particles having an average particle diameter of 48 μm, an aqueous ethanol solution (50% by mass of water and 50% by mass of ethanol) as a jetting liquid, and a Z-Printer 310 Plus (available from 3D Systems Corporation (formerly Z Corporation)). The lamination pitch was set to 100 μm.

A 3D (three-dimensional) design drawing and photographs of the produced formed body are shown in FIGS. 5 and 6.

(8) Evaluation of Bone Regeneration (8-1) Construction of CBE3 Freeze-Dried Sponge The upper and lower portions of the freeze-dried gelatin powder obtained in the description of "Freeze-dried gelatin powder" in the foregoing section of (1) Production of gelatin powder were excised to obtain a porous body having a thickness of 1.5 mm. The porous body was heated in a nitrogen atmosphere at 135° C. for 28 hours to prepare a sponge for evaluation of implantation.

(8-2) Construction of CBE3 Formed Body (Without Pores) (Thermal Crosslinking of 28 Hours: Acid Residual Percentage After 3 Hours is 78%) and CBE3 Formed Body (with Pores) (Thermal Crosslinking of 28 Hours: Acid Residual Percentage in 3 Hours is 82%) p CBE3 formed body (without pores) and CBE3 foamed body (with pores) each having a diameter of about 4.3 mm and a thickness of about 1.7 mm as shown in FIG. 5 were constructed.

(8-3) Evaluation of Bone Regeneration

Evaluation test of bone regeneration was carried out using a CBE3 freeze-dried sponge (thermal crosslinking of 28 hours: acid residual percentage in 3 hours is 95%), a CBE3 formed body (without pores) (thermal crosslinking of 28 hours: acid residual percentage after 3 hours is 78%), and CBE3 formed body (with pores) (thermal crosslinking of 28 hours: acid residual percentage in 3 hours is 82%).

CBE3 freeze-dried sponge, CBE3 laminated formed body (without pores), or CBE3 laminated formed body (with pores) was transplanted into rats and after 4 weeks, micro computed tomography (CT) analysis and pathological analysis were carried out.

The transplantation of the sponge or the formed article was carried out as described below in accordance with the description of Example 1 of WO2011/027850A. As experimental animals, Sprague-Dawley (SD) rats (male, 10 to 12-week old, 0.3 to 0.5 kg) were used. The animals were anesthetized by intraperitoneally administering 0.8 ml/kg of pentobarbital (Nembutal (registered trademark), available from Dainippon Sumitomo Pharma Co., Ltd.). A parietal bone of the rat was exposed, and a circular bone defect portion having a diameter of 5 mm was constructed. Approximately 10 mg of the above sponge or formed body was filled in the constructed bone defect portion, and then the skin was sutured.

Figure 7:
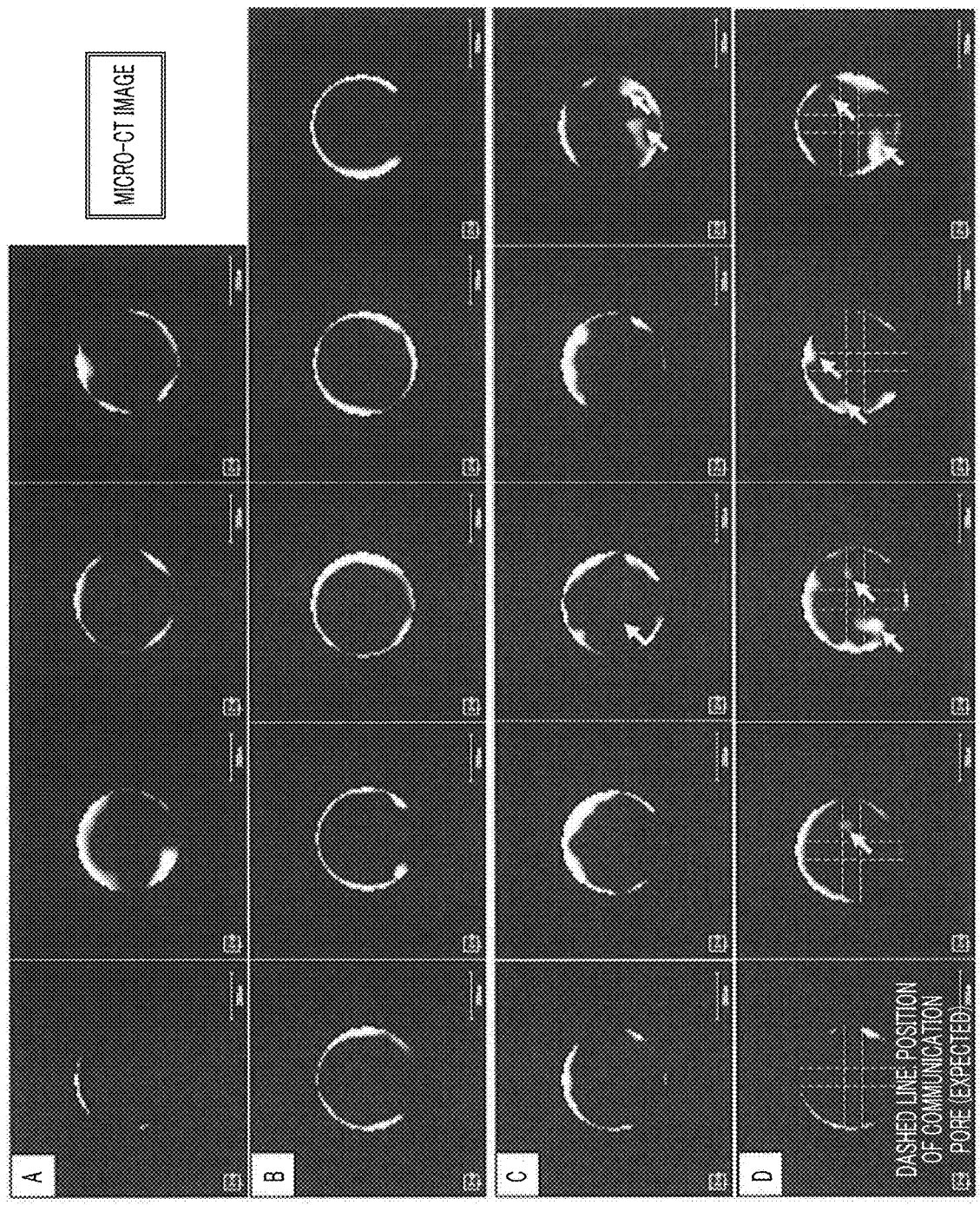
FIG. 7 shows the results of micro-CT analysis for evaluation of bone regeneration.

The results of the micro-CT analysis are shown in FIG. 7. A to D of FIG. 7 show the following.

A: Control (defect only)

B: CBE3 freeze-dried sponge (thermal crosslinking of 28 hours, 95% acid residual percentage in 3 hours)

C: CBE3 laminated formed body (without pores) (thermal crosslinking of 28 hours, 78% acid residual percentage in 3 hours)

D: CBE3 laminated formed body (with pores) (thermal crosslinking of 28 hours, 82% acid residual percentage in 3 hours)

According to the micro-CT analysis, in the case where control (defect only) and CBE3 freeze-dried sponge were transplanted, bone regeneration from the transplanted outer periphery was observed, but bone regeneration as extending from the outer periphery of the CBE3 powder laminate and bone regeneration inside the transplant were not observed. From the above results, the superiority of the CBE3 powder laminate was shown.

(Construction of Pathological Sample)

After the end of the test period, the head was recovered from rats which had been exsanguinated to death, and soft tissues such as skin, eyeball, and brain were removed, followed by decalcification in a hydrochloric acid decalcification liquid. The implantation part was trimmed from the decalcified sample obtained and embedded in paraffin. A 5 μm thick section was cut out from the same embedded sample with a microtome and stained with hematoxylin and eosin.

Figure 8:
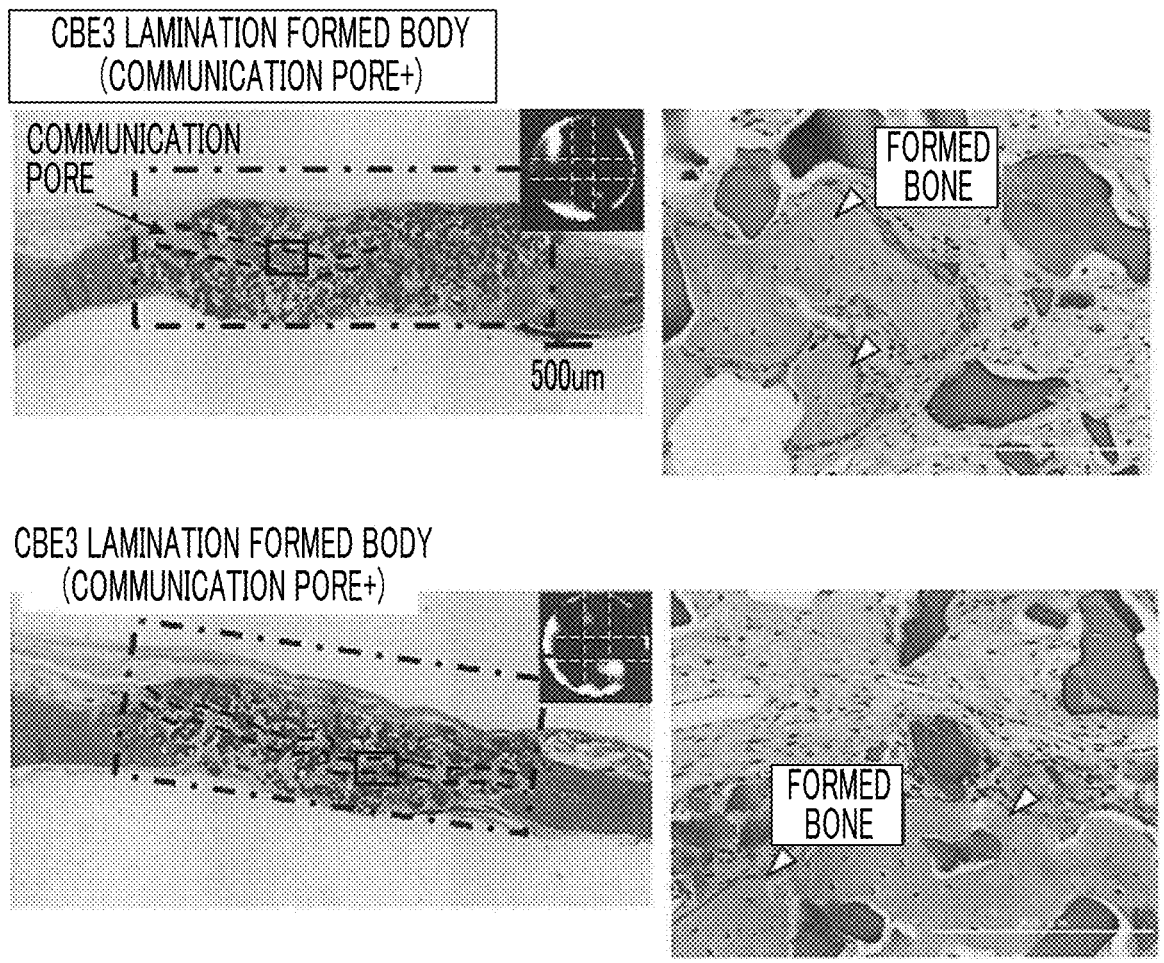
FIG. 8 shows the results of pathological analysis for evaluation of bone regeneration (formed article with communication pores).

The results of the pathological analysis are shown in FIGS. 8 to 10. Soft tissue permeation was observed between CBE3 particles stained reddish violet, indicating good communicative properties of the formed body. In addition, numerous luminal structures were observed in soft tissues, indicating good vascular invasion. The pathological analysis also confirms bone regeneration inside the transplanted CBE3 powder laminate. The cells on the regenerated bone surface were thickened, and therefore it was also observed that bone formation was activated.

(9) Measurement of Void Volume

The filling rate of the gelatin formed body used in the section of (8) Evaluation test of bone regeneration was measured as follows.

Figure 11:
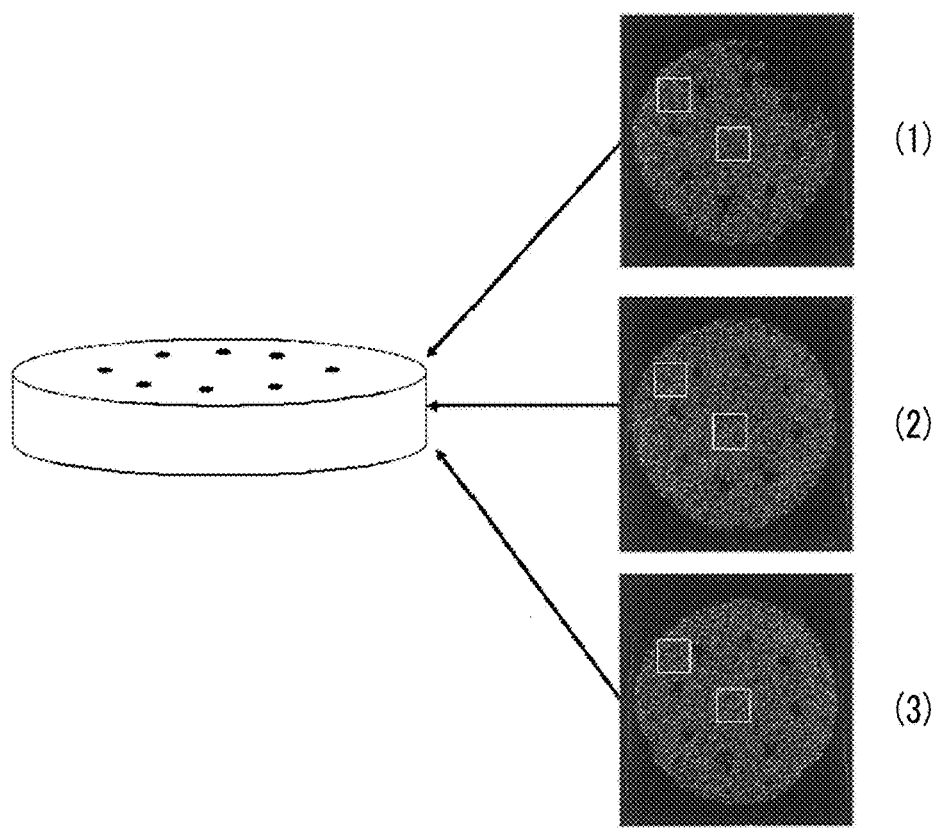
FIG. 11 is a diagram relating to a method of measuring the filling rate of a gelatin formed body.
Figure 12:
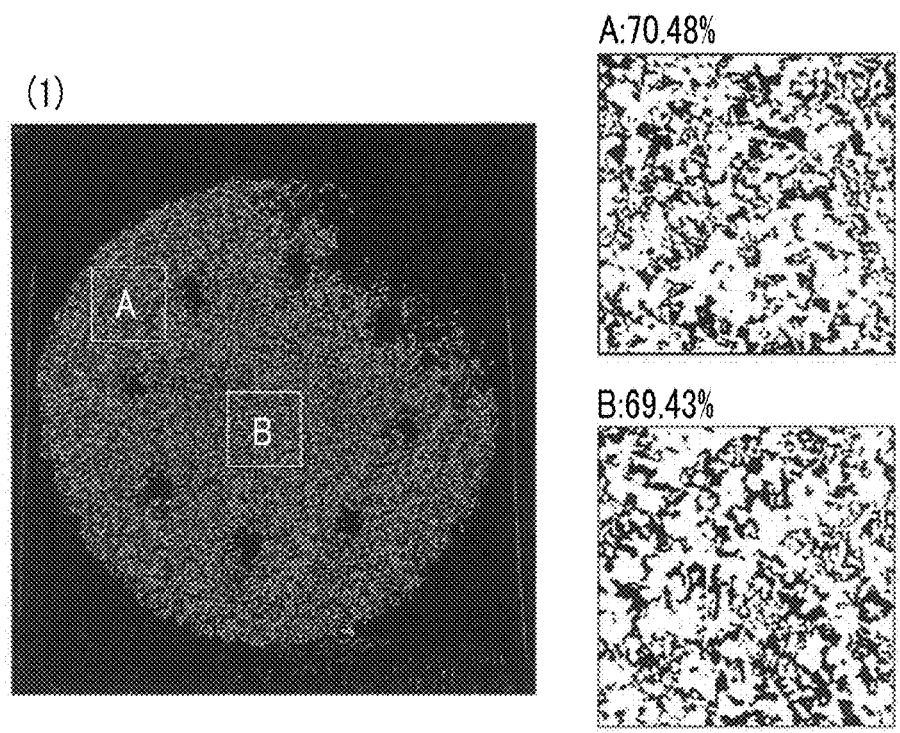
FIG. 12 shows the measurement results of the filling rate of a gelatin formed body.

A CBE3 powder laminate (gelatin formed body) of a disk having a diameter of 20 mm and a thickness of 3 mm was subjected to microfocus CT analysis, whereby a filling rate was measured for the upper, middle, and lower positions in the thickness direction 2 points each position, 6 points in total (FIG. 11). The measurement results of the filling rate are shown in FIGS. 12 to 14. From the measured filling rate, the void volume can be obtained in accordance with the following equation.

$$\text{Void volume}=100\%-\text{filling rate}$$

The void volume of the gelatin formed body was about 30%.

In the freeze-dried sponge, the void volume is higher. Normally, it is assumed that the higher the void volume, the easier the cell enters into the inside of the formed body, and the higher the evaluation result is. However, the gelatin formed body produced by the method according to the embodiment of the present invention exhibited excellent evaluation results even at a low void volume.

In the case of two dimensions, it is considered as a mathematical percolation theory that a path is generated both in the vertical direction and in the horizontal direction in the case where the dots (colored dots in the case of FIG. 15) as the basis of the path become 50% to 60% or more.

In the case of three dimensions, the path can be set to about 30%.

In the formed body in which the CBE3 powder was laminated, it was confirmed in the micro-CT analysis that the formed body has a communication pore structure having a void volume of 30% in which pores having a diameter of about 100 μm are three-dimensionally connected to one another (FIG. 16). This is considered to be the cause of cell permeation even in the case of using a formed body without pores in the rat test. This void is thought to be due to the bulk density determined by the balance between adhesion force and mass of CBE 3 particles.

Reference Example 1

Liquid droplets of water (colored slightly to make it easy to see) or a 50% by mass aqueous ethanol solution were landed on the gelatin powder. FIG. 20 shows the state immediately after dropping of the liquid droplets and two minutes after dropping of the liquid droplets.

In the case of water, permeation is not observed even after 2 minutes or even after 1 hour. After about 1 hour, gelatin dissolved from the gelatin powder entered the water liquid droplets and became jelly-like to pinch on the surface of the gelatin powder.

In the case of a 50% by mass aqueous ethanol solution, permeation was observed within 1 second after landing of the liquid droplets. The permeation was extremely fast.

Reference Example 2

Using pure water as a jetting liquid (ink), and fish gelatin powder (average particle diameter: 54 μm) as a powder, a formed body was constructed with a Z-Printer 310 Plus under the following conditions.

Coating amount: The dot pitch is estimated to be 300 dpi of the head nozzle pitch. There are about 300 nozzles.

Z pitch: estimated to be 100

Pattern: 40 mm (X: main scanning)×30 mm (Y: sub-scanning)×5 mm (lamination)

Figure 21:
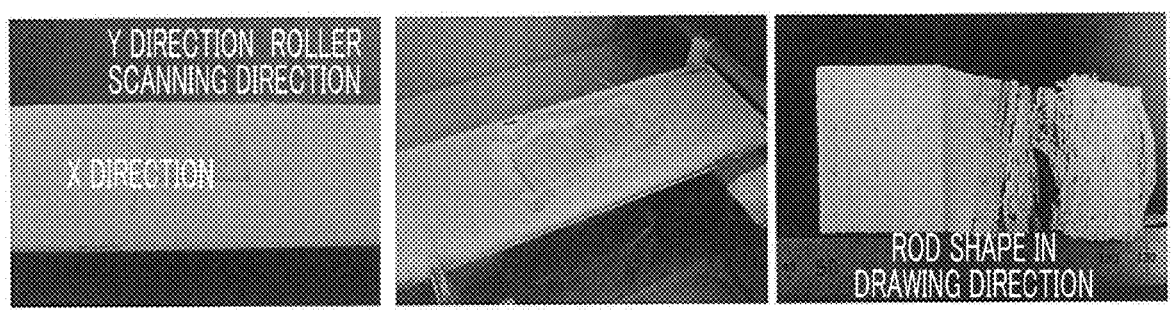
FIG. 21 shows a result of producing a formed body made of a laminate using water as a jetting liquid.

The results of the construction are shown in FIG. 21.

The first five layers in 50 layers were not structured simply by forming large liquid droplets. The first 15 layers out of 50 layers were greatly displaced by recoating. In the case where an anchoric underlayer is formed in the powder, drawing and lamination are made comparatively cleanly, but small deviations have accumulated in the roller scanning direction. The formed body had a strength enough to be lifted, but began to collapse in the case of being touched a little.

[Sequence Listing]

International Application No. 17F00529 under Patent Cooperation Treaty, METHOD FOR PRODUCING GELATIN FORMED BODY AND GE, JP17021124 20170607-00220631451701206335 Normal 201706071423342017-05221124589350_P1AP101_17_1.app

What is claimed is:

1. A method for producing a gelatin formed body which consists essentially of gelatin, the method comprising:
air-drying an aqueous gelatin solution to obtain an air-dried gelatin solid;
pulverizing the air-dried gelatin solid by a dry pulverization method to obtain a powder that has an average particle diameter of 25 to 200 μm wherein the powder consists essentially of gelatin;
a step a of forming, on a substrate, a layer containing the powder;
a step b of jetting liquid droplets of an aqueous solution containing alcohols having a boiling point of 120° C. or lower toward the layer formed in the step a from a nozzle and flying the jetted liquid droplets so that the liquid droplets are landed on the layer formed in the step a, thereby forming a gelatin formed body; and
removing the gelatin formed body from the substrate;
wherein the gelatin has a molecular weight of 10,000 to 90,000 DA.

2. The method for producing a gelatin formed body according to claim 1, wherein the gelatin in the step a is animal gelatin or recombinant gelatin.

3. The method for producing a gelatin formed body according to claim 1, wherein the alcohol having a boiling point of 120° C. or lower in the step b is ethanol.

4. The method for producing a gelatin formed body according to claim 1, further comprising: after the step b,
a step c of forming a layer containing a powder which is obtained by air-drying an aqueous gelatin solution and has an average particle diameter of 25 to 200 μm on the layer formed in the step a and the gelatin formed body formed in the step b; and
a step d of jetting liquid droplets of an aqueous solution containing alcohols having a boiling point of 120° C. or lower from a nozzle and flying the jetted liquid droplets so that the liquid droplets are landed on the layer formed in the step c, thereby producing the gelatin formed body that is removed from the substrate.

5. The method for producing a gelatin formed body according to claim 4, wherein the gelatin in the step c is animal gelatin or recombinant gelatin.

6. The method for producing a gelatin formed body according to claim 4, wherein the alcohol having a boiling point of 120° C. or lower in the step d is ethanol.

7. The method for producing a gelatin formed body according to claim 1, wherein in the step b, the produced gelatin formed body is in contact with the substrate.

8. The method for producing a gelatin formed body according to claim 1, further comprising: after the step b,
a step c1 of forming a layer containing a powder which is obtained by air-drying an aqueous gelatin solution and has an average particle diameter of 25 to 200 μm on the layer formed in the step a and the gelatin formed body formed in the step b; and a step d1 of jetting liquid droplets of an aqueous solution containing alcohols having a boiling point of 120° C. or lower from a nozzle and flying the jetted liquid droplets so that the liquid droplets are landed on the layer formed in the step c1, thereby producing a gelatin formed body; and
further comprising, after the step d1, a step e of forming a layer containing a powder which is obtained by air-drying an aqueous gelatin solution and has an average particle diameter of 25 to 200 μm on the layer formed in the step c1 and the gelatin formed body formed in the step d1; and a step f of jetting liquid droplets of an aqueous solution containing alcohols having a boiling point of 120° C. or lower from a nozzle and flying the jetted liquid droplets so that the liquid droplets are landed on the layer formed in the step e, thereby producing the gelatin formed body that is removed from the substrate,
wherein, in the step b, the produced gelatin formed body is in contact with the substrate,
in the step d1, the liquid droplets are landed on a region corresponding to the outer peripheral region of the upper surface of the gelatin formed body formed in the step b, and
in the step f, the liquid droplets are landed in a region corresponding to the outer peripheral region of the upper surface of the gelatin formed body formed in the step d1 and in a region inside the region surrounded by the gelatin formed body formed in the step d1.

9. The method for producing a gelatin formed body according to claim 1, further comprising a step g of removing the powder not used for forming a gelatin formed body.

10. The method for producing a gelatin formed body according to claim 9, further comprising a step h of heating the formed body to cure the formed body, after the step g.

11. The method for producing a gelatin formed body according to claim 10, wherein the formed body is heated for 1 hour to 72 hours.

12. The method for producing a gelatin formed body according to claim 1, further comprising a step i of encapsulating the gelatin formed body with a support.

13. The method for producing a gelatin formed body according to claim 1, further comprising a step j of seeding cells into the gelatin formed body.

14. The method for producing a gelatin formed body according to claim 1, wherein the gelatin formed body is a scaffold for regenerative medicine or a tissue repair material.

* * * * *